United States Patent [19]

Self

[11] Patent Number: 4,598,042
[45] Date of Patent: * Jul. 1, 1986

[54] IMMUNOASSAY WITH AN INCREASING CYCLIC DETECTION SYSTEM

[76] Inventor: Colin H. Self, 46 Lensfield Road, Cambridge CB2 1EG, United Kingdom

[*] Notice: The portion of the term of this patent subsequent to May 1, 2001 has been disclaimed.

[21] Appl. No.: 559,489

[22] Filed: Dec. 8, 1983

Related U.S. Application Data

[63] Continuation of Ser. No. 307,600, Oct. 1, 1981, Pat. No. 4,446,231, which is a continuation-in-part of Ser. No. 193,647, Oct. 3, 1980, abandoned.

[30] Foreign Application Priority Data

Oct. 3, 1979 [GB] United Kingdom ............... 7934376

[51] Int. Cl.$^4$ ............... G01N 33/54; G01N 33/543; C12Q 1/42; C12Q 1/32
[52] U.S. Cl. ............... 435/7; 435/810; 435/21; 435/26; 436/518; 436/536
[58] Field of Search ............... 435/7, 26, 188, 21, 435/810; 436/518, 536, 537

[56] References Cited

U.S. PATENT DOCUMENTS

| | | | |
|---|---|---|---|
| 3,654,090 | 4/1972 | Schuurs et al. ............... | 435/188 |
| 3,879,262 | 4/1975 | Schuurs et al. | |
| 4,134,792 | 1/1979 | Boguslaski et al. | |
| 4,230,797 | 10/1980 | Boguslaski et al. ............... | 435/810 |
| 4,233,402 | 11/1980 | Maggio et al. ............... | 435/7 |
| 4,277,560 | 7/1981 | Gray et al. ............... | 436/807 |
| 4,307,188 | 12/1981 | White ............... | 435/4 |
| 4,318,980 | 3/1982 | Boguslaski et al. ............... | 435/810 |
| 4,366,242 | 12/1982 | Neumann et al. ............... | 435/7 |
| 4,446,231 | 5/1984 | Self ............... | 435/7 |

FOREIGN PATENT DOCUMENTS

| | | |
|---|---|---|
| 0005271 | 11/1979 | European Pat. Off. |
| 1363565 | 8/1974 | United Kingdom |
| 1433783 | 4/1976 | United Kingdom |
| 1536396 | 12/1978 | United Kingdom |
| 1548741 | 7/1979 | United Kingdom |
| 1550320 | 8/1979 | United Kingdom |
| 1552607 | 9/1979 | United Kingdom |
| 2021262 | 11/1979 | United Kingdom |

OTHER PUBLICATIONS

Anggard et al., "Prostaglandins: Enzymatic Analysis" Science, 163, pp. 470-480 (1-31-1969).

O. H. Lowry, et al., "The Measurement of Pyridine Nucleotides by Enzymatic Cycling", J. Biological Chem., vol. 236, No. 10, 1060, pp. 2746-2755.

E. Pitkanen, "The Hydrolysis of Nicotinamide Adenine Dinucleotide Phosphate by Serum Alkaline Phosphatase", Enzyme, vol. 12, 1971, pp. 226-234.

*Primary Examiner*—Thomas G. Wiseman
*Assistant Examiner*—John Edward Tarcza
*Attorney, Agent, or Firm*—Jacobs & Jacobs

[57] ABSTRACT

An immunoassay uses an antibody or antigen -enzyme conjugate which converts a precursor to a cycling agent used in a cycling detection system. The amount of cycling agent is continually increased permitting amplification. The prefered system converts NADP to NAD using the conjugate label and the cycling system interconverts NAD and NADH.

33 Claims, No Drawings

IMMUNOASSAY WITH AN INCREASING CYCLIC DETECTION SYSTEM

This is a continuation of Ser. No. 307,600, filed 10/1/81, U.S. Pat. No. 4,446,231, which is a continuation-in-part of my earlier U.S. patent application Ser. No. 193,647 filed Oct. 3, 1980, abandoned.

The present invention relates to assays which use a reagent that is enzyme-linked.

Various methods are available for the detection and/or identification of substances in, for example, samples of body materials. Immunoassays make use of the specificity of the reaction of an antigen with its antibody for the detection of substances which are antigenic or can be made antigenic or, conversely, are antibodies or derivatives thereof. Immunoassays may be used for the detection of any substance of any origin provided it falls within one of the above categories, and are particularly useful for testing samples of body materials for the detection of various types of substances, especially naturally occurring substances, for example, hormones, the content of which may change under certain circumstances, for example, pregnancy; substances which may be present in the body under certain circumstances but which are not normally present, for example, particular tumour antigens specifically associated with malignant states; and non-naturally occurring substances, for example, certain drugs.

As indicated above, immunoassays may also be used for the detection of antibodies rather than antigens, for example, in autoimmune diseases and certain cancers, and also to detect certain infectious diseases which give rise to altered specific antibody titres in affected individuals. In the latter case, the disease may be detected and, if desired, its course followed while present in the individual to monitor, for example, response to treatment, or previous infection may be detected, for example, in the testing for rubella.

Immunoassays may be used for qualitative or quantitative determinations. Colour reactions and precipitation reactions, for example, using latex particles for visualisation, are often used in qualitative methods to indicate the presence or absence of the substance under investigation.

In quantitative assays, one of the components is usually labelled in some way, for example, with a radioisotope or with a fluorescent group. Radioactive labels have a number of disadvantages, however, including the cost and complexity of measuring equipment (when compared with colourimetric assays), health hazards associated with radioisotopes, the real limit to sensitivity caused by the degree to which radioisotopes may be incorporated in antigens and antibodies and the inevitable decay of the label on storage.

Similarly, fluorescent labels also require expensive equipment for their determination, and have the further disadvantage that immunofluorescent assays are particularly difficult to standardise and to quantitate. The assessment of results is very subjective and can result in an unacceptable degree of variation among workers.

Other physical and physico-chemical methods are also available for the detection of further types of labels for antibodies and antigens, but these often have limited applicability and again require specialised and expensive apparatus.

Attempts have been made to get round the problems associated with radioisotope and fluorescent labels by the use of enzymes as labels. The enzymes previously proposed have been chosen for their ability to catalyse reactions which are relatively easy to measure and which also proceed at a high rate (cf. Engrall, E. and Perlmann, P., (1972). The Journal of Immunology 109, 129). The enzymes proposed are, for example, those which generate a coloured end product or which produce a substrate for a second enzyme, which substrate is used up in the generation of a coloured end product.

There is, however, the problem of introducing the enzyme label in a high enough concentration and also the problem that simply attaching an enzyme to an antibody or an antigen may result in a certain loss of catalytic activity. The number of labelled molecules to be detected may be relatively small, so it is important that the label can be detected easily.

As indicated above, immunoassays utilise the specificity of the interaction between antibodies and antigens to detect and/or determine these substances. There are, moreover, other analogous pairs of substances that have an analogous specificity for each other; these are the receptors that occur in the body, often in association with cells, and their complementary partners. There is considerable overlap between antibodies and antigens and other ligands and receptors, e.g. a substance that is an antigen may also be the partner for a non-antibody receptor. Moreover, it has proved difficult to distinguish some lymphoid cell receptors from antibody molecules. Examples of partners for non-antibody receptors are substances produced by the body itself, for example, hormones, opiates, and chemical intermediates in the nervous system, and materials originating externally, for example, viruses and toxins. These receptors and their partners recognise each other and bind specifically with one another in the same manner as do antibodies and antigens, and they can be used in assays that are directly analogous to immunoassays for the detection and/or determination of either partner.

The present invention is based on the observation that the enzyme used as the label in an immunoassay or analogous assay may be an enzyme that produces, directly or indirectly, a substance that is capable of influencing a catalytic event without itself being consumed during the catalytic event.

The invention accordingly provides a method for determining a ligand or receptor, which comprises carrying out an assay for the ligand or receptor, the assay requiring a labelled component, wherein the labelled component is a conjugate between (i) a ligand or a receptor and (ii) a primary enzyme that is itself capable of producing or removing a modulator (as hereinafter defined) for a secondary system or that is the first enzyme in an enzyme system that is capable of producing or removing a modulator (as hereinafter defined) for a secondary system, and determining that portion of labelled component to be determined by allowing the primary enzyme and any other enzymes in the enzyme system, to produce or remove the modulator for the secondary system, allowing the secondary system to function in the presence or absence (as appropriate) of the modulator, and determining a product of the secondary system. By producing or removing as appropriate the modulator, amplification is achieved by the production of substantially more than one molecule of product of the secondary system per molecule of modulator.

The terms "ligand" and "receptor" are used in the present Specification to denote a complementary pair of substances that are capable of recognising the specific spatial and charge configuration of each other and of binding specifically with each other.

Ligands are, for example, antigens, haptens, and the partners of cell- and non-cell associated, non-antibody receptors, and receptors are, for example, antibodies and non-cell and cell-associated non-antibody receptors. The term "non-antibody" receptors as used herein includes non-antibody receptors obtained from natural sources and those produced synthetically or semi-synthetically, and also includes analogues thereof that are capable of binding to the appropriate partner. Similarly, their respective partners may be obtained from natural sources, or may be synthetic or semi-synthetic, or analogues of natural partners provided that they are capable of binding to the appropriate receptor.

The antibody component of an antibody-enzyme conjugate of the invention may be any immunoglobulin obtained from any source, provided that it is suitable for taking part in the desired assay. In some cases, it may be preferable to use a heterogeneous antibody population, for example, as obtained from a whole blood sample, whereas in other cases it may be preferable to use monoclonal antibodies. Furthermore, there may be used mixed antibodies, that is to say, antibodies having light and heavy chains originating in different molecules, the mixed antibodies being produced by hybridisation.

It will be appreciated that, instead of being bound to a complete immunoglobulin molecule, the enzyme may be bound to a suitable immunoglobulin fragment. Accordingly, the term "antibody" when used herein denotes any immunoglobulin molecule or any fragment of an immunoglobulin molecule containing an intact antigen binding site and being capable of being bound to the enzyme without substantially interfering with the antigen binding. Examples of suitable immunoglobulin fragments are Fab and $(Fab^1)_2$ fragments.

The antigen component of an antigen-enzyme conjugate of the invention is any antigen that is capable of being bound to the enzyme without substantially interfering with its antibody binding capacity. The term "antigen" when used in the present specification includes haptens, and "antigen-enzyme conjugate" includes haptenenzyme conjugate, unless otherwise indicated.

The term "modulator" is used herein to denote a substance that gives rise to a catalytic event but to which there is no net consumption during the catalytic event.

The term "enzyme" is used herein to denote a particular enzyme activity. (An enzyme may have the form of a discrete molecule or an enzyme complex which may display more than one enzyme activity.)

The term "primary enzyme system" is used in the present specification to denote a system that comprises an enzyme conjugate of the invention and that is capable of producing or removing a modulator for the secondary system. The primary enzyme system may comprise the primary enzyme as the only enzyme, or it may comprise a series of enzymes of which the primary enzyme is the first.

The term "secondary system" is used herein to denote a reaction or reactions modulated by the product of the primary enzyme system, that is to say, the primary enzyme system produces or removes a substance that, in the presence of the secondary system, gives rise to a catalytic event without being consumed (in net terms) during the catalytic event. An example of a type of modulator that may be produced by the primary enzyme system is an enzyme activator, and enzyme inhibitors are an example of another group of modulators. In the latter case, the primary enzyme system must be capable of removing an inhibitor to "switch on" the secondary enzyme system.

In some cases, the primary enzyme system may be capable of simultaneously producing an activator for a secondary enzyme system and of removing an inhibitor therefor.

An example of a further type of modulator is a substrate or cofactor for a secondary system that is capable of regenerating the substrate or cofactor. Such a secondary system involves a cycle. The modulator "switches on" the cycle, which can then continue to turn almost indefinitely, provided there is a sufficient supply of the appropriate substrates. The cycle comprises two or more reactions, at least one of which may be enzyme catalysed. The other reaction(s) in the cycle may each be enzyme catalysed or not.

The modulator may be physically separated from the secondary system, for example, it may be present in a cell or vesicle. In this case, the primary enzyme system produces the modular by causing all or some of the modulator to become available to the secondary system, for example, by causing the cell or vesicle to rupture or become permeable.

The use in assays of the enzyme conjugate of the invention circumvents many of the problems and disadvantages encountered with radioactive and fluorescent labels, and has advantages over previously proposed uses of enzymes as labels, for example, the sensitivity of the assay is improved and the product of the primary enzyme system is not consumed in the reaction for the determination of the label.

By producing or removing a modulator for the secondary system, eg. by producing an activator and/or removing an inhibitor for the secondary enzyme system, or by producing a regeneratable substrate or coenzyme for the secondary enzyme system, or a regeneratable substrate or cofactor for a non-enzymic system, amplification is achieved. Each molecule of modulator results in the production of substantially more than one molecule of product of the secondary system. The modulator produced or removed by the primary enzyme system can be regarded as a catalyst for the secondary system, eg, the presence of an activator or removal of inhibitor "switches on" an enzyme, and a regeneratable substrate or cofactor "switches on" a secondary cycle which can then continue to turn with determinable product being produced at each turn of the cycle. This is in direct contrast to those previous proposed enzyme labels for immunoassays where the enzyme bound in an enzyme conjugate either produces a determinable product directly or produces a substrate for a further enzyme reaction in a simple linear, usually 1:1, ratio. The amplification serves to increase the sensitivity of the assay directly by causing the production of larger numbers of determinable molecules than would be produced directly by ligand or receptor bound enzyme, and thus helps to overcome one of the disadvantages of the previously proposed use of enzymes, that is to say, the tendency to inactivation of certain enzymes on conjugation.

A further advantage is that the reactions involving the primary enzyme system and the secondary system may be carried out separately. This gives greater flexibility with regard to the time and place at which the reactions are carried out. It is also generally easier to quantitate the secondary system if the reactions are carried out separately from those of the primary system. Moreover, there is greater freedom in the choice of enzymes for the secondary system as there can be used in this system enzymes that are not suitable for conjugation to a ligand or receptor, for example, a secondary enzyme system may comprise an insoluble enzyme or an unstable enzyme.

As indicated above, the primary enzyme system used in the method of the invention may comprise the primary enzyme, that is to say, the enzyme present in the conjugate, as the only enzyme, or it may comprise more than one enzyme, only the primary enzyme being bound to a ligand or receptor with each other enzyme generally producing the substrate for the next enzyme. It may be preferable to use a reaction chain as short as possible, for example, using the primary enzyme only to produce or remove the modulator for the secondary enzyme system.

A secondary enzyme system, too, may comprise one or more enzymes. In the case of activation and/or inhibition, there may be only one enzyme in the secondary enzyme system, or the modulated enzyme may be part of a chain or cycle comprising other enzymes and/or non-enzyme catalysed reactions. When the modulator is a regeneratable substrate or cofactor, a cycle is involved. As indicated above, a cycle may comprise at least one enzyme catalysed reaction, or any one or more of the reactions in the cycle may be not catalysed by an enzyme ie a cycle may be wholly chemical; wholly enzymic; or part chemical, part enzymic.

There may be used a secondary enzyme system in which one secondary enzyme produces a substance that is modulatory for a further enzyme, so an extra multiple amplification step is incorporated in the system. Further modulated enzymes and/or modulator-producing enzymes may be used in series.

A secondary enzyme system may be a mixed system comprising enzymes subject to different types of modulation, eg. one or more enzymes subject to activation and/or inhibition, and a cycle capable of regenerating a substrate or coenzyme. This, too, may result in multiple amplification.

The choice of primary enzyme system and secondary system are, of course, linked, as the primary enzyme system must be capable of modulating the secondary system.

Dealing first with the secondary system, this may comprise an enzyme system that is subject to regulation, either by activation or by inhibition. The enzyme system may be naturally subject to regulation or may have been modified to become so. Alternatively, a secondary enzyme system may be capable of regenerating a substrate or cofactor (coenzyme) that is produced by the primary enzyme system and also causing concommitantly the build-up of a substance that is detectable either directly or indirectly. The use of secondary system that generates modulator in this manner is highly advantageous as it may be employed to give rise to a particularly rapid build up in the determinable substance.

A modulator for a secondary system may be natural or synthetic, and a "pre-modulator" may be converted by the primary system into a modulator by removal of the protecting moiety eg. protecting groups or protecting peptides. A natural modulator may have been modified such that it is inactive until acted upon by the primary enzyme system. Metal ions are modulators for some enzymes. A compartmentation system as described below may be used with metal ions.

The secondary system preferably produces a determinable substance or uses a substrate that can be readily determined directly, for example, spectrophotometrically, by colour, by staining, manometrically, by light production eg using ATP on firefly extract, or microbiologically eg by using bacteria with specific nutritional requirements, or by measuring physicochemical changes, eg. conductance changes. The determinable substance produced may, however, be determined indirectly, by acting as the substrate for one or more further reaction(s) producing a readily determinable end product or may be a regulator for a further reaction. An enzyme system may, for example, catalyse a reaction in which carbon dioxide is produced eg. using pyruvate decarboxylase; in which the oxygen tension is changed, eg. using glucose oxidase with measurement by an oxygen electrode; or in which DNP-hydrazine can be used to produce a coloured end product. It is particularly convenient to utilise an enzyme system capable of producing NAD or a compound that can partake in a reaction in which NAD/NADH interconversion is involved. (Abbreviations used in this specification are set out before the Examples.)

Some examples of primary enzyme systems comprising one enzyme only with associated secondary enzyme systems also comprising one enzyme only are given in Table I below, by way of example only:

TABLE I

| Primary enzyme | Secondary enzyme |
|---|---|
| 1. Enzyme that produces cyclic AMP eg. adenylate cyclase | Enzyme subject to activation by cyclic AMP eg. phosphorylase B kinase, pyruvate carboxylase, phosphoenol pyruvate kinase |
| 2. Glyoxylate reductase (reduces glyoxylate) | Isocitrate dehydrogenase (inhibited by mixture of glyoxylate and oxaloacetate) |
| 3. Enzyme that removes ATP, especially that converts ATP to ADP eg. ATPase eg. apyrase | Enzyme inhibited by ATP, especially when also activated by ADP eg. isocitrate dehydrogenase |
| 4. Glutathione reductase (produces glutathione) | Glyoxylase (activated by glutathione) |
| 5. Fumarase or fumaryl acetoacetate lyase (produce fumarate) | Mitochondrial NAD-linked malic enzyme (activated by fumarate) |

In the examples given above, the primary enzyme system comprises one enzyme only. As indicated previously, however, the primary enzyme system may comprise several enzymes, only the first being bound in a conjugate. An example of such a system, with a single enzyme in the second system, is given below:

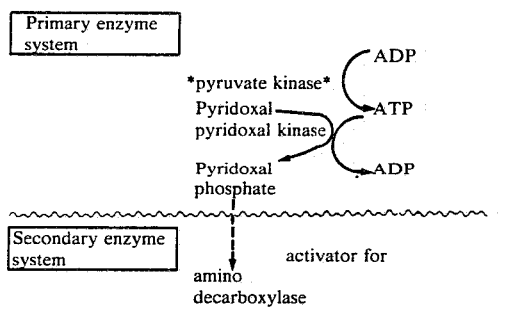

A further example of such a system is the following:

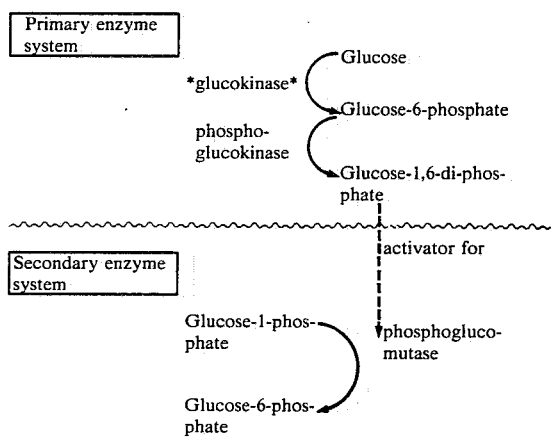

(For this method, the phosphoglucomutase must be in the de-phosphorylated condition. The enzyme can be dephosphorylated by exposing it to fluoride ions.)

In all diagrams,** denotes the primary ie. conjugated enzyme, and there are given only those components of the various reactions that are necessary for the understanding of the reaction schemes.

As indicated previously, a secondary enzyme system may comprise only one enzyme, or it may comprise several enzymes, more than one of which may be subject to regulation by a modulator, if desired. An example of a system comprising a chain of reactions in the secondary system is the following:

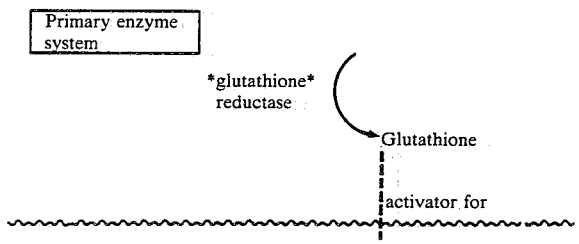

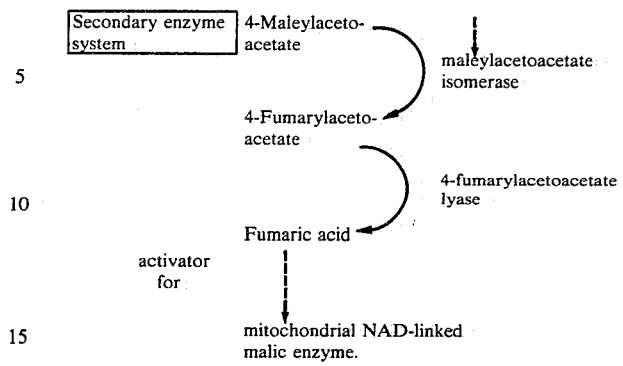

-continued

In this case, the product of the primary enzyme system is the modulator for the first enzyme in the secondary enzyme system, and extra multiple amplification is achieved by the inclusion of a further modulated enzyme in the secondary system.

It may be preferable to use primary and secondary enzyme systems as simple as possible. When more enzymes are incorporated, however, particularly if they are themselves subject to modulation, different advantages may be achieved, for example, with regard to the sensitivity of the assay.

An example of a simple system that can be extended with the addition of extra enzymes is that utilising E. coli Type I pyruvate kinase (PK) as the secondary enzyme system with phosphofructokinase as the primary enzyme. Phosphofructokinase produces fructose-1,6-diphosphate (FDP), which is a very potent activator for E. coli Type I pyruvate kinase (in the presence of certain amounts of phosphoenolpyruvate, cf. M. Malcovati, G. Valentini, H. L. Kornberg, Acta vitamin. enzymol. (Milano) 1973, 27,96.

The system described above can be extended by providing ATP, which is required by phosphofructokinase, indirectly by means of an enzyme capable of converting ATP to ADP, for example, mammalian pyruvate kinase or E. coli Type II pyruvate kinase. Such a system has the advantage that it generates more ATP (the modulator) during the reaction to drive the activator-producing enzyme faster.

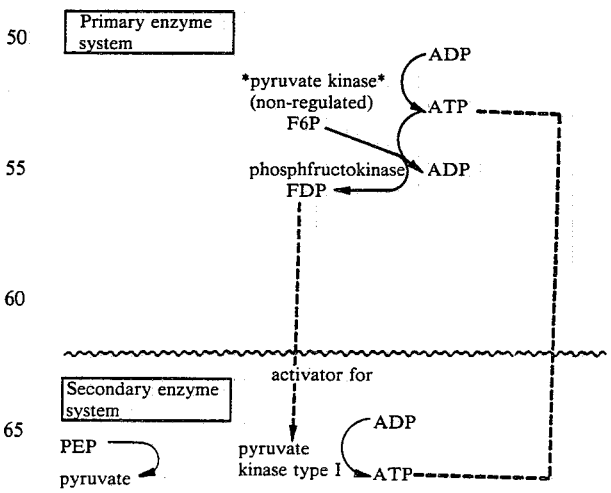

As soon as the primary enzyme (non-regulated pyruvate kinase) produces some ATP, phosphofructokinase is able to produce fructose-1,6-diphosphate (FDP), which in turn activates the FDP-sensitive pyruvate kinase (which is preferably present in relatively high concentrations). This pyruvate kinase, too, converts ADP to ATP which, if both primary and secondary enzyme systems are allowed to react together in one vessel, further increases the production of FDP by phosphofructokinase. This leads to augmented stimulation of the FDP-sensitive pyruvate kinase, and a substantially explosive increase in the production of pyruvate from phosphoenolpyruvate. The pyruvate can be converted to lactate by lactic dehydrogenase, with concommitant oxidation of NADH which can be followed photometrically. Alternatively, the pyruvate can be reacted with DNP-hydrazine to give a coloured end product.

An example of a system in which the modulator, once produced by the primary enzyme system, is self-producing, is that involving the conversion of complement factor C3 to C3b as follows:

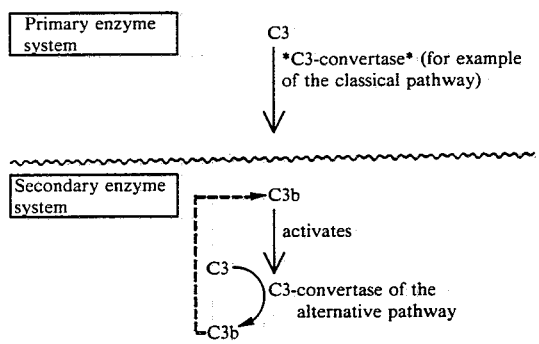

Complement component C3 is cleaved proteolytically to form the fragments C3b and C3a. There are two distinct C3-convertases which can do this: that of the so-called classical pathway of complement activation and that of the alternative pathway. Significantly, the latter is unlike the former in that it requires C3b itself to function.

In the reaction scheme shown above, the C3b formed by the independent C3-convertase, in activating the dependent convertase, results in an increase in the formation of C3b. This positive feed-back system would operate until maximal activation was achieved and very much more C3b was being produced than by the primary system alone. Either C3, C3b, C3a or the biological effects of these mediators in, for example, cell lysis or provocation of anaphylactoid reactions can be followed to indicate presence of the primary enzyme system.

As indicated above, the primary enzyme system may produce a regeneratable substrate for a secondary system. In this case, a secondary enzyme system may comprise two or more enzymes. Preferably one of the enzymes produces or uses a substance that is readily determinable. A two-enzyme system is, for example, as set out schematically below:

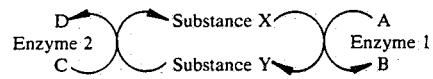

Substance X is the product of the primary enzyme system. The secondary enzyme system should be selected so that there is build-up of at least one of B and D and-/or a decrease in at least one of A and C (insofar as they exist), as X recycles via Y. Provided suitable amounts of A and C are present, substance X will be continually recycled, using one molecule of each of A and C per cycle and producing one molecule of each of B and D. At least one of A, B, C and D is preferably readily determinable itself or may participate in one or more further reactions to give a determinable product or to use a determinable substrate. More than two enzymes may be combined in larger cycles or in interconnecting cycles. Alternatively, substance Y may be the product of the primary enzyme system. (In either case, the cycle may be reversed, if desired.)

An example of a system described in general terms above is that in which the secondary enzyme system comprises fructose diphosphatase and phosphofructokinase.

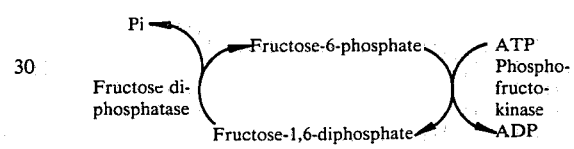

It is possible to determine the production or consumption of any of ATP, ADP and inorganic phosphate (Pi).

The primary enzyme system for the above secondary enzyme system should be one that is capable of producing either frutose-6-phosphate or fructose-1,6-diphosphate. Fructose-6-phosphate may be produced by a primary enzyme system in which phosphoglucomutase is the primary enzyme, converting glucose-1-phosphate to glucose-6-phosphate, which is then converted by phosphoglucoisomerase to fructose-6-phosphate. Fructose-6-phosphate may also be produced from glucosamine-6-phosphate by glucosamine-6-phosphate deaminase. Fructose-1,6-diphosphate may be produced from glyceraldehyde-3-phosphate and dihydroxyacetone phosphate by the action of aldolase, to enter the cycle at the bottom.

A further example of a cofactor cycle used in a secondary enzyme system is one following:

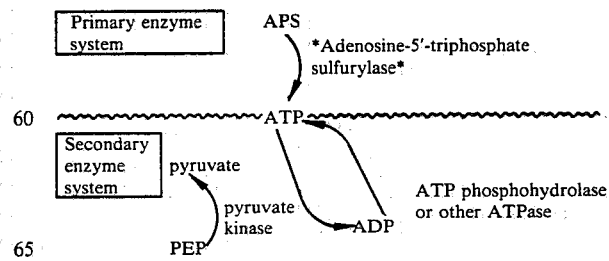

(Adenosine-5'-triphosphate sulfurylase converts adenosine-3'-phosphate-5'-phosphosulphate to ATP and SO₄.) Alternative enzymes for the production of ATP in the primary system are, for example, pyruvate phosphate dikinase, which catalyses the following reaction: PEP+AMP+pyrophosphate→pyruvate+ATP+Pi, and ATP:D-ribose-5-phosphate pyrophosphotransferase, which converts AMP and 5-phosphoribose-1-pyrophosphate to ATP and D-ribose-5-phosphate.

This system may be modified and extended, providing an example of a system involving both a cofactor cycle and a modulated enzyme:

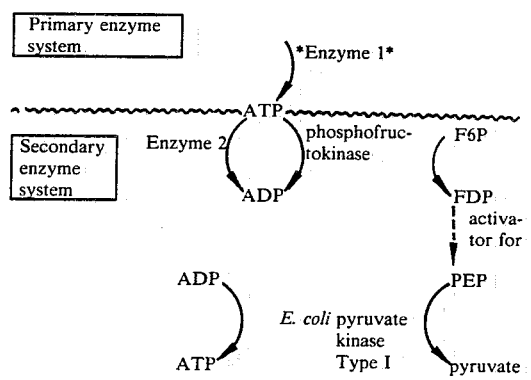

Enzyme 1: see above
Enzyme 2: phosphoglycerate kinase or non-regulatory pyruvate kinase The third reaction is preferably carried out separately from the second reaction.

Systems involving regenerated substrates are directly analogous with systems involving regeneratable cofactors (coenzymes).

An example of such a system is the following, in which NADP is the regeneratable coenzyme:

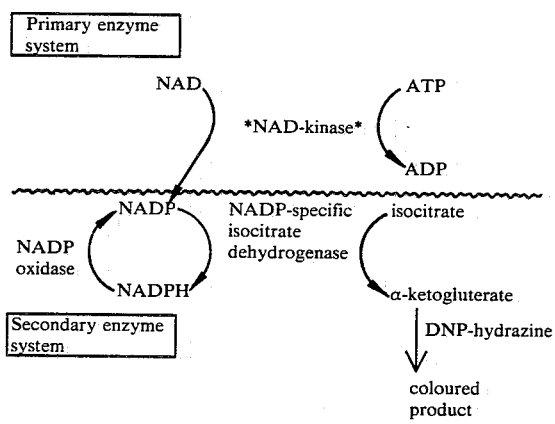

As mentioned above, a modulator, for example, a substrate or coenzyme, may take part in a secondary enzyme cycle in which not all the reactions are enzyme-catalysed. A simple example of such a system is as follows:

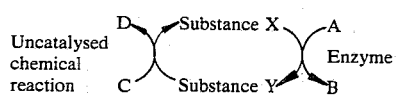

Either substance X or substance Y may be the product of the primary enzyme system. An advantage of such a system is that it may be possible to use a total of only two enzymes: one in the primary enzyme system and one in the secondary system.

An example of a group of reactions that may participate in such a cycle are oxidation-reduction reactions, for example, involving NAD/NADH or NADP/NADPH interconversions. An example of such a cycle is given below:

$$\text{Uncatalysed chemical reaction} \quad \underset{C}{\overset{D}{\diagdown}}\underset{NAD(P)H}{\overset{NAD(P)}{\diagup\diagdown}}\underset{B}{\overset{A}{\diagup}} \text{Enzyme}$$

Substances capable of reduction with concomitant oxidation of NAD(P)H are well known, for example, 3'-(4,5-dimethylthiazolyl-2)-2,5-diphenyltetrazolium (MTT tetrazolium) is particularly useful, because on reduction it gives a blue coloured product and, moreover, the results are linear with regard to the NAD(P). A secondary enzyme cycle involving an NAD(P)/NAD(P)H interconversion may therefore be determined directly.

In the case of secondary enzyme cycles involving NAD(P)/NAD(P)H interconversions, it is preferable to use a primary enzyme system capable of producing NAD or NADP, for example, NADP may be produced from NAD by NAD-kinase, and NAD may be produced from NAD-dihydroxyacetone+nicotinamide by NADase (DPNase). Examples of such cycles are given below:

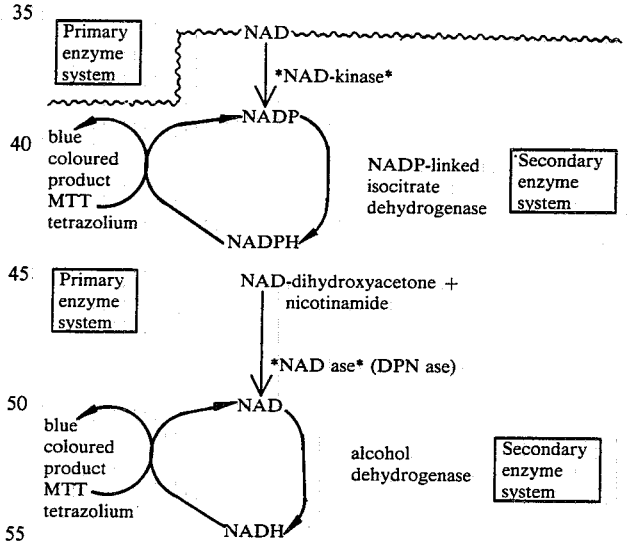

A modulator may moreover, take part in a secondary system that does not comprise any enzymes. In such a case, the modulator is a substrate or cofactor for a cycle in which the modulator is regenerated, so there is no net consumption thereof (cf the wholly and partly catalysed cycles mentioned above).

A possible example of such a cycle is that in which the primary enzyme is peroxidase, which removes iodine (in the form of iodide ions) from thyroxine. The iodide ions may then be recycled in the secondary system via iodine, eg as follows:

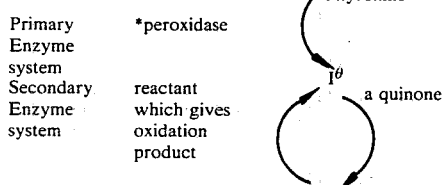

Alternatively, use may be made of a system using an iodide-iodine cyclic reaction (see Clinical Chemistry principles and Techniques, R. J. Henry, Harper & Row, New York 1964, p.7) as follows:

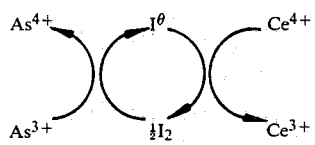

As indicated above, the modulator may be physically separated from the secondary system, the primary enzyme system causing the modulator to become available. The modulator may be an activator or inhibitor or an regeneratable substrate or co-factor. Metal ions are examples of modulators that may be compartmentalised. Metal ions are modulators for a number of enzymes, for example $Mg^{2+}$ and $Mn^{2+}$ are modulators for pyruvate kinase and isocitrate dehydrogenase.

The modulator may be present in relatively high concentrations in, for example, a synthetic or semi-synthetic vesicle or an organelle or cell, or may simply be present in a normal cell. The primary enzyme system may rupture or lyse the vesicle or cell, or may simply make it more permeable, to the modulator at least, so that there is leakage of sufficient amounts of modulator to affect the secondary system.

The use of lysozyme and trypsin may be particularly suitable for the disruption of cells, organelles, and vesicles. Either lysozyme or trypsin may be bound in the desired conjugate with the other being present in the reaction medium for disruption of the structure. In general, the trypsin is preferably bound in the conjugate, with higher concentrations of lysozyme in the reaction medium.

Lysozyme itself is capable of lysing the microorganism *Micrococcus lysodeiktus*. This microorganism may therefore be used as such or may have its internal concentration of a modulator increased, to be ruptured as desired by a primary enzyme system comprising lysozyme as the primary enzyme.

The method of the invention may be used for detecting ligands and receptors of natural or non-natural origin. Immunoassays have wide application, in both clinical and non-clinical fields; they are particularly useful in any circumstance where it is necessary to detect and/or determine small or very small amounts of substances. Clinical uses include, for example, the detection and/or determination of blood group substances, of Australia antigen, of diseases of various microbial origins eg. diseases caused by viruses, bacteria or fungi, or parasitic diseases, of hormones, of substances that may be present under certain conditions, for example, during pregnancy, for example, pregnancy-specific proteins and foetal proteins in foetal material and even in maternal material eg. blood, or in association with certain malignant states, of antibodies associated with autoimmune diseases and certain cancers, and drugs. Immunoassays are particularly useful in forensic investigations, as the amounts of substances to be detected and/or determined is often very small. Drug detection, both in forensic investigations and in investigations associated with human and animal sporting events may be advantageously carried out by immunoassays. The method of the invention may be used for detecting any of the above substances, and also any other substance that can be detected and/or determined by an immunoassay.

Assays analogous to immunoassays, for the detection and/or determination of ligands and receptors other than antigen/antibody pairs are also useful clinically and otherwise. Such ligands are, for example, hormones, for example, insulin, glucagon, piuitary hormones eg. vasopressin, oxytocin and trophic hormones, steroid hormones and gastric hormones; chemical intermediates and signals in the nervous system, for example, acetylcholine, opiates and their analogues, naloxones and encephalins, chalones, developmental signals and cell interaction signals; other naturally occurring chemicals eg. histamine; and substances originating outside the body eg. viruses and toxins.

An assay for a substance that can be considered to be both an antigen and the partner for a non-antibody receptor may be carried out using either the corresponding antibody or the other receptor as partner. An immunoassay may have the advantage that the antibody can be obtained more readily and cheaply than the other receptor. Conversely, it may be difficult to raise an antibody to a particular antigen, in which case the use of the non-antibody receptor is preferable. An assay using a non-antibody receptor may be even more specific than an assay using an antibody against the corresponding ligand because a specific receptor generally binds at the active part of the ligand molecule, whereas the corresponding antibody usually binds at another part of the molecule, giving greater possibility of cross-reactions.

Antibodies and antigens have a specific affinity for each other; when, however, an antibody-antigen complex has been formed, this complex and complement factor C1q can form a ligand-receptor pair. Factor C1q may therefor be used in an assay of the invention to detect antibody-antigen complexes of any type.

The assay technique to be used in the method of the invention is any immunoassay or analogous technique in which a labelled ligand or receptor is used as one of the components. The assay may be qualitative, quantitative or semiquantitative. Such assay techniques are well known, and include, for example, competitive binding techniques, so-called "sandwich" techniques, and any modifications thereof, for example, techniques which use competitive binding and "sandwich" techniques together in one assay. (The term "sandwhich" techniques as used herein includes so-called "anti-globulin" assays.)

In a competitive binding assay there is, for example, competition between the unknown amount of one component and a standard amount of the same component for a standard amount of its complementary component. One of the known components is generally bound to a solid matrix, whereby it can be readily isolated and one of the known components is generally labelled in some way.

In one method of carrying out a competitive binding assay, a calibration curve may first be set up as follows:

An antigen is bound to a solid matrix and then allowed to come into contact with a solution containing its specific antibody. The antibody is then taken out of solution onto the matrix, and if the antibody or antigen is labelled, measurement of label of the material on the matrix gives a measure of the amount of specific antibody-antigen combination that has taken place. This combination may be interfered with in a modification of this method, by first mixing the antibody with the same, but soluble, antigen. If a large excess of soluble antigen is used the antibody binds this and thus remains in solution with its specific antigen-binding sites saturated and therefore unable to bind with matrix-linked antigen. Substantially no labelling will then appear in specific association with the solid matrix. Less than saturating amounts of soluble antigens will result in more free antibody available for combination with matrix-linked antigen. The system can therefore be calibrated in terms of soluble antigen and then used to determine quantitatively amounts of antigen present in "unknown" samples.

Alternatively, the assay may be organised conversely such that the amount of antibody remaining in solution after the addition of matrix-bound antigen is that which is quantitated.

Assays using a ligand and a non-antibody receptor are carried out in a directly analogous manner, using the ligand as the antigen and the receptor as the antibody.

Generally, "sandwich" techniques are based on the following: one component of an ligand-receptor couple, (generally bonded to a solid matrix), is contacted with the sample containing an unknown amount of the component to be determined. This, bound to the first component (and generally matrix-linked via the first component), is determined by the use of a further sample of the first component (which has been labelled in some way, and is not matrix bound), or a third component that has specific affinity for the component to be determined and that is itself labelled. (The chain may be longer than this.)

In a "sandwich" assay using a ligand and non-antibody receptor, either the ligand or the receptor may be matrix-bound. If the receptor is matrix-bound, then a further sample of that receptor may be used after the ligand has been bound thereto, or a mixed assay may be carried out, ie. the receptor is matrix-bound, the ligand is bound thereto, and then labelled antibody against the ligand, is used to detect the bound ligand.

"Sandwich" techniques have certain advantages over competitive binding techniques, for example, further amplification may be achieved because there will often be more than one receptor site for the conjugated enzyme to bind, so more than one molecule can bind per molecule of substance to be determined, thus increasing the sensitivity of the assay.

A further advantage of sandwich techniques is that it may be possible to use a standard enzyme conjugate, which may simplify the determination and is often more convenient when carrying out assays for different substances. An example of a system using a standard conjugate is that in which a sheep antibody against the antigen to be determined is bound to a solid matrix, the antigen to be determined is then contacted with the sheep antibody, free antigen is removed, a goat antibody against the antigen is contacted with the antigen, free antibody is removed, and finally a standard labelled antibody with specificity for the antigenic determinants on goat antibodies is contacted with the goat antibody.

After an assay has been carried out according to the chosen technique or mixture of techniques, it is usually necessary to separate the portion of enzyme conjugate that is to be assayed from the portions of enzyme conjugate that are present in the assay reaction mixture but are not to be assayed. This is facilitated by the conjugate being bound, during the assay, to an insoluble matrix.

The matrix may be, for example, Sephadex, a plastics material eg. nylon, cellulose or a derivative thereof, for example, bromoacetylcellulose (cf. Self et al, loc cit). Some receptors, both antibodies and other receptors, may be cell-associated in vivo; some antibodies are present on cell surfaces, some receptors are also associated with cell surfaces, and some receptors are present inside cells. Cell-associated receptors of any type may be used after isolation and purification, or they may be used in association with all or part of the cell ie. already matrix-bound.

Generally, the matrix-bound conjugate is assayed, but that portion of the conjugate left in suspension may be assayed.

The enzyme bound in the conjugate is then generally allowed to catalyse the appropriate reaction. If two or more reactions are required to modulate the secondary system, these may be carried out simultaneously or successively as separate reactions, in each case in situ or in different reaction vessels. The reaction(s) catalysed by the secondary system may also be carried out simultaneously with those of the primary enzyme system (ie. on modulation by the primary enzyme system) or as separate reaction(s) and may be carried out in situ or in another reaction vessel.

It is often preferable to allow the primary enzyme system to react for a predetermined time, and then to allow the modulator to contact the secondary system for a predetermined time. As mentioned above, separating the primary and secondary systems makes it more easy to obtain quantitive results and gives greater freedom in the choice of enzymes.

It is also possible, in some cases, to release the primary enzyme from the enzyme conjugate after the portion of enzyme conjugate to be assayed has been isolated, for example, if the enzyme is bound in the conjugate by disulphide bonds, it may be released by the action of dithiothreitol. If this is done, the free enzyme is reacted subsequently as described above for enzyme conjugates.

In general it is preferred to have the secondary system primed, that is to say, to have all the components present in optimal amounts and under optimal reaction conditions so that the presence or removal of the appropriate modulator will result in an immediate and optimal reaction. In some cases, however, it may be desirable to delay the action of the secondary system. This may be done by not combining the product of the primary system (the modulator) with the secondary system, or by omitting one or more of the components of the secondary system. Addition of the missing component will then initiate the reaction.

A conjugate of the invention may be bound to a micro-titre plate, a test strip or dip stick. In the former case, the whole reaction sequence may be carried out on the plate. Microtitre plates are well known in the art, and ones suitable for application in previously proposed enzyme immunoassays (Elisa, or Enzyme-linked Immunosorbent assays) are available commercially. Test strips and dip sticks are also known.

In the method of the present invention, the enzyme conjugate may be determined in situ ie. each of the reactions, starting with that catalysed by the primary enzyme, may be carried out on the micro-titre plate.

Test strips and dip-sticks may be used analogously to micro-titre plates.

A kit comprising components suitable for carrying out an immunoassay of the invention is also part of the present invention.

A conjugate of the invention may be prepared by any method suitable for binding ligands and enzymes or receprors and enzymes. Such methods are well known and often utilise bifunctional agents. The two components are preferably bonded such that the ligand-receptor binding sites on ligands and receptors are not substantially impaired, and also that the active site of the enzyme is not inactivated.

As has been explained hereinbefore, the modulator for the secondary system may serve to activate the secondary system by its production or serve to activate the secondary system by its removal if it is an inhibitor. Of these two alternative methods it is generally most desirable that the modulator activates the secondary system when it is produced by the primary system. Thus a favoured method of this invention comprises carrying out an assay for the ligand or receptor, the assay requiring a conjugate between the ligand or receptor and a primary enzyme that is itself capable of producing a modulator for a secondary system and determining that portion of labelled component to be determined by allowing the primary enzyme to function so that said modulator is produced, whereby the secondary system is caused to function, and determining a product of the secondary system.

As previously indicated herein the method of this invention is particularly suitable when adapted for the determination of an antigen. Also as previously indicated herein the method of this invention is particularly suitable when adapted for the determination of an antibody.

As previously indicated the amplification achieved in the method of this invention occurs because the secondary system produces substantially more molecules of detectable substance than are produced by the primary system once it is "switched on" by the primary system. Particularly rapid rises in the presence of the detectable product of the secondary system can occur when the secondary system is capable of regenerating a substrate or co-factor (i.e. a modulator) for the secondary system that is produced by the primary enzyme system. This aspect of the invention in which the modulator is a substrate or co-factor for a secondary system that is capable of generating the substrate or co-factor is particularly favoured. Yet more favourably in this form of the invention the secondary system comprises a cycle capable of generating the substrate or co-factor. Systems which can be adapted to favourable purposes include (a) a primary system comprising phospofructokine and a secondary system comprising pyruvate kinase type I and (b) a primary system comprising phosphofructokinase and non-regulated pyruvate kinase and the secondary system comprises pyruvate kinase type I.

As hereinbefore indicated the modulator may be generated in this invention in (a) a secondary system comprising one enzyme catalyzed reaction and one nonenzyme catalyzed chemical reaction (b) a secondary system that does not comprise any enzyme catalyzed reactions or (c) a secondary system comprising two enzyme catalyzed reactions.

As previously indicated particularly apt systems for use in this invention comprises oxidation/reduction systems, of which those employing NAD/NADH interconversions and NADP/NADPH interconversions are most suitable.

As made apparent hereinbefore, the method of this invention is most aptly performed using systems in which the secondary systems has all components present except the modulator in optimal amounts before the modulator is allowed to control the secondary system. (In this aspect the modulator will not be an inhibitor).

Desirably the oxidation/reduction system employed is one interconverting NAD and NADH. A preferred modulator in such a system is NAD which most aptly is produced from NADP by a conjugate between a ligand or receptor and a phosphatase.

In one aspect this invention provides a method for determining a ligand or receptor which method comprises carrying out an assay for the ligand or receptor, the assay requiring a labelled component wherein the labelled component is a conjugate between a ligand or a receptor and a phosphatase capable of producing NAD which is a modulator for a secondary system which interconverts NAD and NADH and determining that portion of labelled component to be determined by allowing the conjugate between the ligand or receptor and phosphatase to produce NAD, allowing the secondary system to function in the presence of the NAD, and determining a product of the secondary system.

Since this form of my invention relies upon the production of NAD (the modulator for the secondary system) by the action of a conjugate of a phosphatase, the skilled worker will appreciate that the assay will be carried out in the presence of NADP. Schematically therefore the latter part of the assay may be represented thus:

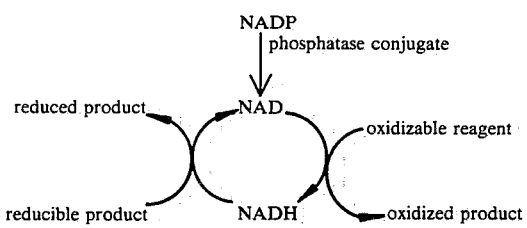

Either the oxidized product or the reduced product may be determined during this assay. I believe that one of the considerable advantages of this amplified assay is that it allows for the detection of a product by eye or by the use of simple optical measuring devices. One particularly suitable method of producing an optically detectable colour change is to employ MTT tetrazolium (also known as thiozolyl blue or 3-(3,4-dimethylthiazolyl-2)-2,5-diphenyltetrazolium) which on reduction can change from a yellow colour to a dark colour (for example a blueish/greyish/blackish colour). Thus a favoured reducible reagent for use is MTT tetrazolium. This reagent often produces a more marked colour change in the presence of an electron transfer reagent such as PES (also known as phenazine ethosulphate).

A favoured oxidizible reagent for use in the NAD/NADH cycle is an alcohol such as ethanol which can be oxidized by alcohol dehydrogenase into an oxidized product such as acetaldehyde.

From the foregoing the skilled worker will appreciate that a more detailed representation of the preceeding schematic representation may be written thus:

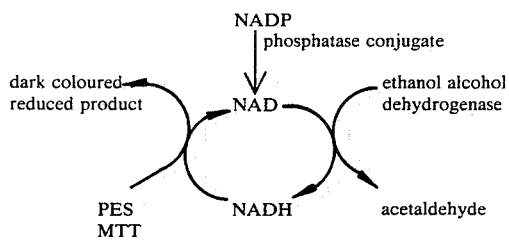

Once the preceding primed cycle is switched on by the production of NAD by the primary cycle, a colour change (by eye or machine) can be detected. Clearly the system will utilize NAD-free reagents since the modulator should not be introduced except by the action of the phosphotase conjugate on the NADP.

The phosphatase conjugate may be from any convenient source. The phosphatase may be of the alkaline type or the acid type. The phosphatase may be bound to a ligand or receptor using any convenient method such as by reaction with a bifunctional conjugating reagent such as SPDP (N-succinimidyl-2'-(2-pyridyldithio)propionate or other like agent.

The skilled worker will appreciate that such methods of conjugating enzymes are well known in the art. Most desirably the phosphatase is conjugated to an antibody or an antigen. Preferably the phosphatase is conjugated to an antibody. The antibody may be an antibody against any antigen including those instances where the antigen is another antibody.

From another aspect, this invention provides a method of determining a conjugate between a ligand or receptor and a phosphatase which method comprises contacting said conjugate with NADP and the components of a NAD/NADH cycle other than NAD or NADH and determining a product of that cycle.

Most suitably the ligand and receptor are an antibody or antigen although other moieties are envisaged, for example a drug and its receptor.

From another view, this invention provides a method of determining a conjugate between an antibody or antigen and a phosphatase which method comprises contacting said conjugate with NADP and the components of a NAD/NADH cycle other than NAD and NADH and determining a product of that cycle. Naturally the method will be carried out under conditions such that when NAD is produced by the conjugate the cycle will operate. Since sufficient amounts of the reagents required to drive the cycle will be present an amplification is achieved that greatly increases the sensitivity of the detection method. Normally the reagents employed are in sufficient excess so that their concentrations do not limit the amplification achievable.

Most aptly the conjugate employed is a conjugate of alkaline phosphatase since it has been discovered that the optimal pH for the cyclic reactions is very suitable for the operation of alkaline phosphatase (pH 8–10.5, more aptly 9–9.5 for example 9.3). This allows one to cause the primary reaction and the cycle to proceed simultaneously if desired. If a conjugate of acid phosphatase is used the initial reaction is generally carried out at pH 4–6, for example 5.6. At this pH the cycle does not work efficiently so that when the pH is raised to allow the cycle to operate the acid phosphotase is effectively switched off and produces no further NAD. This has the advantage that simpler kinetics and easier quantification can be achieved.

Alkaline pH values as outlined above may be achieved using conventional buffers such as an ethanolamine/HOi buffer. Acid pH values as outlined above may also be achieved using conventional buffers such as a citrate buffer (buffers of both types may be obtained from commercial supplies such as Sygma or the like).

The assays of this invention may be carried out at any non-extreme temperature such as 5°–45° C. but generally it is preferred to carry out the assay at ambient temperatures.

Most desirably this invention provides a method of amplifying an enzyme linked immunoabsorbent assay (ELISA) system which utilizes a phosphatase linked to a ligand or receptor wherein the amplification is achieved by using the phosphatase linked to a ligand or receptor to produce NAD from NADP which NAD starts a NAD/NADP cycle one product of which is determinable.

The reagents and products of this amplified system may be as hereinbefore described.

ELISA systems which may be amplified in this manner include those adapted to the detection of: Malaria; Amoebiasis; Schistomosiasis; Onchocerciasis; Toxoplasmosis; Hydatidosis; Trichinella; Babesia; Leishmaniasis; Trypanosome; Cytomegalovirus; Hepatitis B antigen; Measles; Rubella; Plant Viruses; Erythrocyte Antigens; Factor Viii-related antigens; antibodies against rubella, cholera, E.coli; Salmonella O antigen; markers of oncological importance such as alpha-foetoprotein; hormones such as thyroid hormones and sex hormones etc; baculoviruses; gentamicin; etc.

ELISA systems are well known—see for example:

Voller, A & Bidwell, D. E. (1975) Brit. J. Exp. Path. 56:338

Engvall, E & Perlman, P. (1971) Immunochem. 8:871

Voller, A., Bidwell, D., Huldt, G. & Engvall, E. (1974) Bull. Wld. Hlth. Org. 51:209

Carlsson, H. E., Lindberg, A. A. & Hammerstein, S. (1972) Infect. Immun. 6:703

Voller, A, Bidwell, J. E. & Bartlett, A (1976) Microplate Enzyme Immunoassays of Virus Infections—from Manuals of Clinical Immunology, Chapt. 69 (Ed. Rose, N. & Friedman, H), Am. Soc. Microbiol. p506.

Veldkamp, J. & Visser, A. M. (1975) Brit. J. Vener. Dis. 51:227

Voller, A., Bidwell, D. E. & Bartlett, A. (1976) Bull. Wld. Hlth. Org. 53:55

Voller, A., Bidwell, D. E. & Bartlett, A. (1976) The Application of Micro-Plate Enzyme-Linked Immunosorbent Assays to Some Infectious Diseases in The First International Symposium on Immunoenzymatic Techniques INSERM Symposium No 2 (Ed. Feldman et al) North Holland Publishing Co.

An extremely effective ELISA system is presently available as Rubelisa Test Kit from M. A. Bioproducts, Walkersville, Md. 21793, USA. This Test Kit (their cataloque number 30-3000) is a sensitive method for the determination of Rubella virus IgG antibody in human serum. However the method recommends a relatively long final incubation period and the use of a spectrophotometer. Amplification of this test by the method of this invention allows for the reduction of the incubation period and allows visual determination (without the necessary use of a spectrophotometer).

Amplification can be achieved by the method of this invention by inter alia cyclising substrates or alternatively by clyclising cofactors (coenzymes). It is particularly advantageous to cycle NAD and NADH when at least one (preferably NAD) acts as cofactors as hereinbefore described. One of the advantages of this cofactor cycle is its ready ability to be linked to the production of visually detectable changes as hereinbefore described.

The following abbreviations are used in the present specification:

G1P, glucose-1-phosphate;
G6P, glucose-6-phosphate;
F6P, fructose-6-phosphate;
FDP, fructose-1,6-diphosphate;
ATP, adenosine triphosphate;
ADP, adenosine diphosphate;
AMP, adenosine monophosphate;
PEP, phosphoenolpyruvate;
NAD, nicotinamide adenine dinucleotide;
NADH, reduced NAD;
PGM, phosphoglucomutase;
PGI, phosphoglucose isomerase;
PFK, phosphofructokinase;
PK, pyruvate kinase;
LDH, lactic dehydrogenase;
FDPase, fructose-1,6-diphosphatase;
DNP, dinitrophenol;
NADP, nicotinamide adenine dinucleotide phosphate;
NADPH, reduced NADP;
APS, adenosine 3'-phosphate-5'-phosphosulphate.

The following Examples illustrate the invention.

EXAMPLE 1

(a) Preparation of Pyruvate Kinase Extract

Cultures of *E.coli* strain K1-1 were grown on a synthetic medium containing essential nutrients and glycerol as carbon source, until well into their logarithmic phase of growth. The cells were harvested, washed by centrifugation and resuspended in a sonication buffer of 5 mM phosphate, 1 mM EDTA, 2 mM mercaptoethanol pH 7.5 in an amount of approximately 20 mg dry weight per ml. They were then disrupted with an MSE ultrasonic disintegrator for 4 minutes. The resulting crude extract was separated from cell debris by centrifugation. As well as containing pyruvate kinase (PK) this extract also contained an interfering isoenzyme of PK with different properties, and also a number of other enzyme activities which interfered with the determination. It was found, however, that it was possible to remove all of these contaminating activities simply by heating the extract to 55° C. for 20 minutes. This heat-treated extract was used in this Example.

(b) Preparation of the Immunoabsorbent

Bromoacetyl cellulose conjugated human serum albumin BAC-HSA was prepared exactly as described in Solid Phase Assay of Radioactive Antibody to Soluble Antigens by Self, C. H., Tew, J. G., Cook, R. G. and Stavitsky, A. B. (1973) in Immunochemistry, 11, 227–233.

(c) Preparation of the Enzyme-Antibody Conjugate

This was based on Protein thiolation and reversible protein-protein conjugation. N-Succinimidyl 3-(2-pyridyldithio) propionate a new heterobifunctional reagent by Carlsson, J., Drevin, H., Axen, R. (1978) in Biochem. J., 173, 723–737.

Both the enzyme (phosphofructokinase "PFK", which had been prepared from Stearothermophilis and purified to crystalline purity by means of AMP and ATP affinity chromatography) and the antibody (IgG, obtained from Miles-Yeda Ltd., Rehovot, Israel), were prepared for conjugation by separate passage through a Sephadex G-25 (fine) column equilibrated with the "coupling buffer" of 0.1M sodium phosphate pH 7.5 containing NaCl at 0.1M. One mg of each protein was applied. One ml of the IgG eluant of optical density at 280 nm of 0.67 O.D. units was taken, shaken gently while a five-fold molar excess of the conjugating agent (N-succinimidyl 2-(2-pyridyldithio) propionate, "SPDP") was added from a stock solution (5 mM) in ethanol. The mixture was allowed to stand for 30 minutes at 23° C. with occasional shaking. Then with rapid stirring, 1 ml of the PFK eluant, also of optical density at 280 nm of 0.67 O.D. units, was added. The mixture was allowed to remain at room temperature for 24 hours. During this time the newly introduced labile disulphide groups on the IgG underwent exchange reactions with the pre-existing reactive thiol groups on the PFK to give rise to PFK-IgG conjugates.

(d) Method of Assay

Into each of two small test tubes were put 20 μl of the PFK-IgG conjugate. Human serum albumin (0.1 ml of a 10 mg/ml solution) was added to one tube and bovine serum albumin (0.1 ml of a 10 mg/ml solution) added to the other. BSA was added to the second tube so that any non-specific protein effect on the conjugate would be duplicated in both tubes. The volumes of the tubes were then made up to a standard 1.0 ml with phosphate-buffered saline (PBS). The contents of the tubes were mixed and incubated at 37° C. for 15 minutes. They were then added separately to two aliquots of BAC-HSA (each 0.1 ml of the standard suspension which had been washed 4 times in PBS) in micro-centrifuge tubes. The capped tubes were then shaken and incubated at 37° C. for a further 15 minutes. They were then centrifuged in a micro-centrifuge at full speed for one minute, the supernatant solution discarded, the solid washed by the addition of 1.5 ml of PBS to each tune, the contents mixed on a vortex mixer and centrifuged as above. The washing procedure was repeated 4 times to ensure removal of unbound contaminating PFK. To each tube was then added 0.94 ml of the assay buffer (10 mM dimethylglutarate pH 6.8, 5 mM, MgCl₂) and then 50 μl of a 40 mM solution of fructose 6-phosphate and 10 μl of a 40 mM solution of adenosine triphosphate. The contents of the tubes were mixed by means of the vortex mixer and then incubated with gentle shaking at 37° C. for two and a half hours. After this the tubes were once more centrifuged at full speed for one minute and the supernatant solutions taken off and assayed for evidence of previous PFK activity in the tubes during the two and a half hour incubation. The particular system enabled a direct comparison to be made between the triggered amplifier method of the present invention and a conventional 1:1 coupled enzymic detection method. For the former, the supernatant solution was tested for its ability to activate a primed PK assay set-up without FDP. For the latter the ADP produced concomitantly with the FDP was assayed by following the NADH oxidation it produced in a directly coupled pyruvate kinase—lactate dehydrogenase system set-up to operate optimally (with added FDP) but without ADP. The two assay systems were, therefore, composed as shown in Table 1.

TABLE 1

Assay components for the ADP and FDP assays

| Component | Primed amplifier (FDP determining) | Conventional coupled (ADP determining) |
|---|---|---|
| NADH | 0.1 mM | 0.1 mM |
| LDH (Lactate Dehydrogenase) | 14.4 units | 14.4 units |
| PK(I) extract | 10 μl | 10 μl |
| PEP§ | 2.0 mM | 2.0 mM |
| ADP | 2.0 mM | NIL |
| FDP | NIL | 1.0 mM |
| ATP | 0.4 mM | 0.4 mM |
| supernatant solution | 100 μl | 100 μl |
| assay buffer | to 1 ml | to 1 ml |

§The maximal amount of PEP was used which could be added without causing unwanted background activation of the pyruvate kinase in the FDP-determining assays.

Results (i) Primed amplifier (FDP-dependent) assy.

This was set up such that full activation of the system produced a rate of oxidation of NADH of 7.9 nmoles/min (a convenient rate to measure).

The results of adding 100 μl of the supernatant solution from the immunoabsorbents either previously exposed to HSA or BSA are shown in Table 2.

TABLE 2

Primed amplifier (FDP-dependent) assay results

| supernatant | rate of NADH oxidation |
|---|---|
| from BSA-exposed tube | 4.8 nmoles/min (61% maximal) |
| from HSA-exposed tube | nil |

(ii) Conventional-coupled (ADP-dependent) assay.

The results of adding 100 μl of either supernatant solution to the ADP-dependent system are shown in Table 3.

TABLE 3

Conventional-coupled (ADP-dependent) assay results

| supernatant | rate of NADH oxidation |
|---|---|
| from BSA-exposed tube | 0.12 nmoles/min (1.6% maximal)§§ |
| from HSA-exposed tube | nil |

§§This figure on repeated assays was close to back-ground and difficult to quantitate accurately.

The results show clearly that:
(a) the PFK-IgG conjugate was inhibited in its binding to BAC-HSA by HSA much more than by BSA.
(b) the sensitivity of the primed-amplifier system was much higher than the conventional-coupled reaction.

EXAMPLE 2

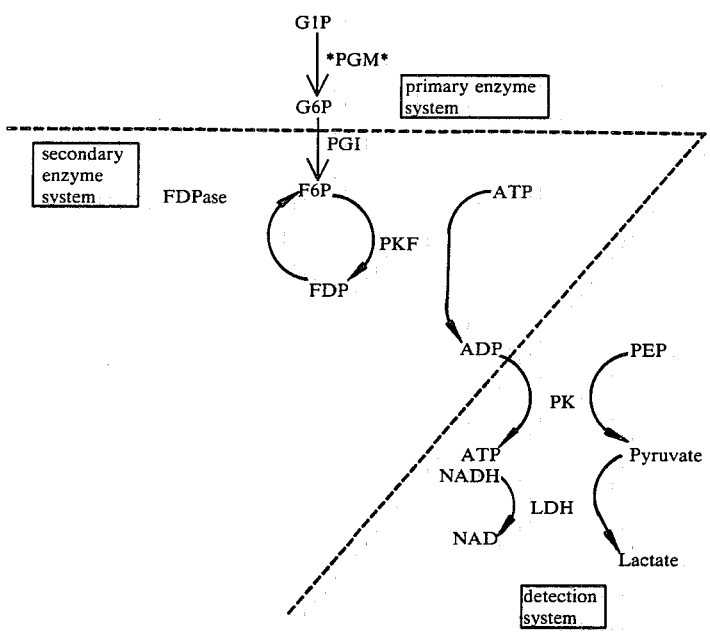

The reaction sequence is outlined above. Phosphoglucomutase (PGM) was chosen to be the enzyme to be linked to an antibody. The presence of the antibody is determinable by the ability of the conjugate to catalyse the formation of G6P from G1P. This in the presence of phosphoglucose isomerase (PGI) results in the sequential formation of F6P which is then itself acted upon by phosphofructokinase (PFK) to give FDP. This latter reaction generates one molecule of ADP from ATP for every molecule of F6P converted to FDP. The final detection system shown in the diagram takes advantage of this, in that it is dependent on ADP. This system results in oxidation of NADH which is monitored spectrophotometrically by the concomitant decrease in optical density of the mixture to ultraviolet radiation of 340 nm.

The secondary enzyme cycle operates as follows. In the presence of fructose diphosphatase (FDPase) the FDP generated by the system, and which otherwise would play no further part in the system, is reconverted into F6P (without involvement of ADP/ATP) and is thus available again for a further turn of the cycle, to give rise to another molecule of ADP for each turn of the cycle.

The amplification of the activity of PGM achieved by the catalytic secondary enzyme cycle may be readily seen by comparing the NADH oxidation resulting from the corresponding 1:1 linked enzyme system which does not have FDPase present ie. in which F6P is not recycled.

Method of enzyme assay

All determinations were performed using 1 ml quartz cuvettes with a path-length of 1 cm. NADH oxidation was monitored by the decrease in absorbance at 340 nm. The reactions were carried out in a buffer comprising: 25 mM Tris-HCL, 10 mM MgCl₂, 1 mM EDTA at pH 8.00 and 30° C. The final reaction mixtures were as shown in Table 4. LDH and PK were obtained from Boehringer Mannheim and the other enzymes from the Sigma Chemical Company

Results of enzyme assays

These are shown in FIG. 4 and represent the activities of the systems after they had been incubated for 12 minutes at 30° C., after initiation.

The results indicate that:

(i) the basic 1:1 linked enzyme reaction sequence worked (compare first to third column), (ii) the catalytic substrate cycle formed by inclusion of FDPase into the system markedly increased the activity of the system for the standard amount of PGM (column two).

(iii) the background activity of the total system, including the substrate cycle, in the absence of PGM is very low (column three).

TABLE 4

| components§ | 1:1 linked (no cycle) | including cycle | no PGM (back-ground) |
|---|---|---|---|
| NADH | 0.1 mM | 0.1 mM | 0.1 mM |
| ATP | 0.4 mM | 0.4 mM | 0.4 mM |
| PEP | 2.0 mM | 2.0 mM | 2.0 mM |
| G1P | 2.0 mM | 2.0 mM | 2.0 mM |
| LDH | 1.1 U | 1.1 U | 1.1 U |
| PK | 0.04 U | 0.04 U | 0.04 U |
| PGI | 0.2 U | 0.2 U | 0.2 U |
| PFK | 0.02 U | 0.02 U | 0.02 U |
| FDPase | NONE ADDED | 0.1 U | 0.1 U |
| PGM | 0.06 U | 0.06 U | NONE ADDED |
| oxidation rate of NADH (n mole/minute) | 0.475 | 4.72 | 0.064 |

'U' stands for units of enzyme activity. However as different conditions were used to measure each enzyme by their various manufactures the various activities do not necessarily correspond to each other in the final assay mixtures but simply denote the standard amounts of each preparation used.
§Assay buffer of 25 mM Tris-Hcl, 10 mM MgCl₂, 1 mM EDTA, at pH 8.00 added to each assay to a final volume of 1.00 ml.

Linking the substrate cycle to antibody-antigen reactions

After demonstrating the amplification afforded by the substrate cycle as above, the usefulness of the system in detecting antibody (or antigen) was assessed. This was done by conjugating the primary enzyme, PGM, to IgG with specificity against human serum albumin.

Formation of the conjugate

As in Example 1, the heterobifunctional linking reagent SPDP was used, however in this instance both enzyme and antibody were treated before conjugation.

One mg of the IgG (Miles-Yeda Ltd) was passed through a Sephadex G-25 column previously equilibrated with the 'coupling-buffer' (0.1M sodium phoshate pH 7.5 containing 0.1M NaCl). The antibody eluted from the column was then shaken gently with a ten-fold excess of SPDP which was added from a 5 mM stock solution in ethanol. The mixture was allowed to stand for 30 minutes at 23° C. with occasional shaking. It was then passed through another Sephadex G-25 column, this time equilibrated with 0.1M sodium acetate at pH 4.5 containing 0.1M NaCl. The protein fraction of the eluant was taken an equal volume of 100 mM dithiothreitol was added with rapid stirring. The mixture was left for 20 minutes at 23° C. after which it was passed through another Sephadex G-25 column equilibrated with the original 'coupling buffer'.

At the same time, 1 mg of PGM was passed through a G-25 column equilibrated with coupling buffer. The major protein band of the eluant was then exposed to a ten-fold excess of SPDP as above and left also for 30 minutes at 23° C. It was then mixed rapidly with the treated antibody and left to stand for 2 hours at 23° C. to allow the conjugate to form.

Full Conjugate Assay

Into each of two small test tubes were put 0.2 ml of the PGM-Igg conjugate. Human serum albumin (0.1 ml of a 10 mg/ml solution) was added to one tube and the same amount of bovine serum albumin to the other; 0.7 ml of phosphate-buffered saline (PBS) was then added to both tubes and the contents mixed and incubated at 37° C. for 15 minutes. They were then added separately to two aliquots of BSA-HSA (each 0.1 ml of the standard suspension which had been washed 4 times in PBS) in micro-centrifuge tubes. The capped tubes were then shaken and incubated at 37° C. for a further 15 minutes. They were then centrifuged in a micro-centrifuge at full speed for one minute, the supernatant solution discarded, the solid washed by the addition of 1.5 ml of PBS to each tube, the contents mixed on a vortex mixer and centrifuged as above. The washing procedure was repeated 4 times to ensure removal of unbound contaminating PGM. To each tube was then added 50 µl of a 40 mM solution of glucose-1-phosphate and assay buffer (25 mM Tris-HCl, 10 mM MgCl₂, 1 mM EDTA, pH 8.00) to a final volume of 1 ml. The contents were mixed and then incubated with gentle shaking for two and a half hours at 37° C. After incubation, the tubes were centrifuged at full speed for one minute and the supernatant solutions taken off with Pasteur pipettes and the contents assayed for evidence of PGM activity during the two and a half hour incubation. They were assayed in two ways. By the direct 1:1 linked enzyme sequence outlined above and also by the sequence including the secondary enzyme cycle (FDPase included). The assays were set up as previously described but included 0.2 ml of the superanatant solutions and thus 0.2 ml less of the separately added assay buffer in each case.

Results

These are shown in Table 5. They show two features:

(i) that the substrate cycle inclusion into the assay provides for much greater activity of the system for a given amount of conjugate.

(ii) that the system is capable of showing the inhibition of uptake of the conjugate onto BAC-HSA by soluble HSA as against the control of BSA.

TABLE 5

Activities of BAC-HSA bound PGM-IgG conjugates in terms of final NADH oxidation (in n moles/minute)

| supernatant | without substrate cycle | with substrate cycle |
|---|---|---|
| HSA-exposed tube | 0.19 | 2.21 |
| BSA-exposed tube | 0.36 | 5.07 |

EXAMPLE 3

Detection of Pyruvate kinase (II)

In order to demonstrate the enhancement in sensitivity brought about by the method of this invention an assay for pyruvate kinase (II) was carried out with and without a secondary system to produce amplification. The two assays may be represented as follows:

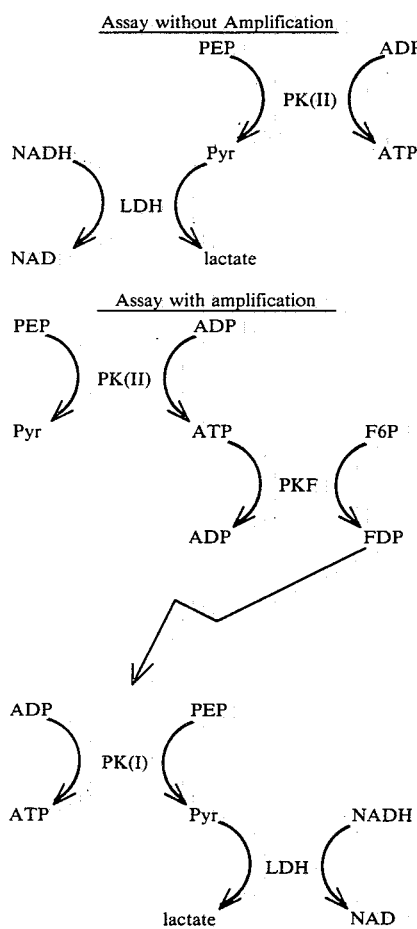

In the assay system without amplification PK(II) converts PEP and ADP into pyruvate and NADH to NAD and lactate. The change in concentration of NADH can be monitored by absorbence at 340 nm.

In the assay system with amplification (that is the assay incorporating the secondary system) the preceeding sequence takes place but in addition the secondary system generates ATP. In this amplified system, in addition to the PEP, ADP, NADH, PK(II) and LDH present in the non-amplified system, the following are also present: F6P, PFK and PK(I). In the presence of ATP (generated by primary cycle) the PFK converts the F6P into FDP. The FDP activates the PK(I) which then is available to convert the PEP and ADP to ATP and pyruvate. The ATP thus produced feeds back within the secondary system and the pyruvate is converted into lactate by LDH in the presence of NADH. This end reaction is monitored at 340 nm as in the unamplified assay.

To indicate the usefulness of this amplification method the PK(II) was initially assayed by the direct reaction as follows: The assay mix was as shown in Table 6 (left column) with a buffer consisting of 10 mM dimethylglutarate pH 6.8 5 mM $MgCl_2$. All assays were carried out at 30° C. The PK(II) was obtained from Calbiochem and, as a result of trials, a standard amount chosen which gave the activity shown in the Table. This amount was used for all following experiments. PK(I) was as in previous experiments.

The assay system including the positive feed-back amplifier was composed as shown on the right hand column of Table 6. The activity attribuatable to the addition of the same amount of PK(II) as before and after allowing the feedback system to get underway for seven minutes, is shown. The activity attribuable to PK(II) is raised eleven times over the direct method.

TABLE 6

|  | Direct assay | Feed-back assay |
|---|---|---|
| ADP | 0.4 mM | 0.4 mM |
| PEP | 1.0 mM | 1.0 mM |
| NADH | 0.1 mM | 0.1 mM |
| LDH | 1.1 U | 1.1 U |
| PK(II) | standard | standard |
| F6P |  | 2.0 mM |
| PFK |  | 1.0 U |
| PK(I) |  | 10 μl |
| Buffer | To 1.0 ml | To 1.0 ml |
| Rate of Change Absorbence (OD Units at 340 nm per 10 minutes) | 0.005 | 0.055 |

Using the direct method, the standard amount of PK(II) could just about be detected whereas it was quite readily detectable using the feed-back amplifier.

In any situation where the PK(II) is used as a label in analogous manner to those used in the Examples hereinbefore the increased overall activity of the secondary system attributable to PK(II) would clearly be of benefit in the detection of material labelled by the enzyme. Thus for example, on labelling antibody against human serum albumen with PK(II), a complex is available for the detection of human serum albumen as a result of the activity of the primary enzyme triggering a secondary sequence which is itself capable of generating modulator for example as described in Example 2.

EXAMPLE 4

Detection of Anti-rubella Antibody

A Rubelisa 96 well plate is taken and labelled as necessary. The wells are washed by filling each with PBS-Tween from a wash bottle and then air bubbles are removed from the wells by moving the plate gently back and forth. The PBS-Tween is shaken from the wells into a disposal receptacle containing a solution of 5% household bleach and each well refilled with PBS-Tween and the air bubbles removed again. The plate is then left for three minutes and then emptied again as above. The whole process is repeated two more times—the final time ensuring complete emptying by tapping the upside-down plate on a clean paper towel.

Reconstituted serum diluent (250 ul) is then added to each well. The patients' individual sera are shaken to homogeneity and then 5 ul of each serum is added to one well containing rubella antigen and also to one well containing control antigen. Serum is withdrawn and expelled three times in the well to help mix it. It is of utmost importance to use different pipettes for different sera. Three control sera (negative, low positive and high positive) are included with each test that is carried out. Three pairs of wells must therefore be used for these controls. If less than three patients' sera are to be tested at any one time it is advised that these can be positioned immediately following the test sera on the plate. However, if the plate is used to its maximum capacity of 45 separate test sera then it is advised that the control samples are distributed on the plate as: high positive—A1 & B1; low positive—C11 & D11; negative—G12 & H12 (5 ul of each). If fewer than 45 patients' sera are tested it is advisable to place them with the high positive at the beginning, the low positive in the middle and the negative at the end of the batch of sera tested. After all of the sera are added the plate is placed on a Micromixer for a few minutes. The plate is placed in a plastic bag with a wet cotton or paper pledget, the bag sealed to allow a humid atmosphere to develop and kept at room temperature (20°–25°) for two hours. The plastic bag is then opened and the liquids are shaken from their wells into the disposal receptacle. The wells are then washed again as described above (with PBS-Tween, four times). Then 250 ul of 50-fold diluted conjugated anti-serum supplied with the kit is added to each well. The plate is incubated as above in the humid bag for a further 2 hours at room temperature, after which the liquid is shaken from the wells into the disposal receptacle and the plate washed again four times as above. The wells are now ready to be assayed for their alkaline phosphatase content. To each well is added 210 ul 0.14M ethanolamine-HCl buffer at pH 9.3 and containing 5 mM $MgCl_2$. The following are added to each well: 10 ul 10 mM thiazolyl blue (MTT), 10 ul of 40 mM phenazine ethosulphate (PES), 5 ul of alcohol dehydrogenase supplied by the Sigma Chemical Company Ltd especially free of NAD (cataloque number A3263) and 5 ul of 1M ethanol. NADP is then added to each well. This is done by adding 10 ul of a 10 mM solution of NADP to each well. Depending on the number of samples being tested and the accuracy required this may be achieved either by adding the solution to each successive well quickly and then mixing on a Micromixer or (with many samples) by adding the solution at fixed intervals (such as a second to minutes) from one well to the next. The reactions are then monitored by observing the colour change of the solutions from pale yellow towards black visually—taking account of any differences in time of addition of the NADP solutions to the various wells.

The solution in the well initially coated with rubella antigen and to which high positive control serum was added will change colour at a much faster rate than the solution in a rubella antigen well to which serum containing significantly less anti-rubella antibody activity was added, and also much faster than the well containing control antigen to which the high positive control serum was added.

If required, the reaction bringing about the colour change can be stopped, after a suitable period (such as minutes to hours—depending on the sensitivity required) for example 5 minutes, by for example changing the pH of the solution. To achieve this the contents of a well can be removed to a vessel, such as a 1.0 ml colourimeter cuvette, containing 0.75 ml of 2M citrate buffer at pH 4.8, the solutions mixed and the degree of previous reaction documented by measuring the degree of colour change from pale yellow to black against a standard chart or by use of a colourimeter set to 570 nm. This alternative has the advantage that the degree of reaction does not have to be documented at the very time it is occurring.

In another alternative, the wells may be assayed for their alkaline phosphatase content by allowing them to first act on a standard NADP solution which is then transfered to another vessel for the colour generating reaction to take place. In this alternative, the NAD concentration is not therefore continuously increasing whilst the colour reaction is taking place and so quantification is somewhat easier. For this, 250 ul of 0.14M ethanolamine buffer at pH 9.3 and containing 5 mM $MgCl_2$ and 0.4 mM NADP is added to each well to be assayed. The plate is incubated at room temperature for a time such as minutes to hours (depending on the sensitivity required) for example 5 minutes. At the end of this period the contents of each well are added to suitable vessels containing 10 ul of 10 mM MTT, 10 ul of 40 mM PES, 5 ul of alcohol dehydrogenase (A3263), 5 ul of 1M ethanol in 0.14M ethanolamine buffer at pH 9.3 sufficient to make the final volume 1.0 ml, and the contents mixed. Again the colour change of the solutions from pale yellow to black is monitored either visually or wth a colourimeter set to 570 nm. The results of these alternative approaches will be found to be in accordance with that stated above i.e. wells initially containing rubella antigen which receive a serum high in anti-rubella antibody, by the method of the test, will give rise to a faster development of black colour than wells which do not meet these criteria.

It is frequently desirable to detect enzymes in liquids in which a number of reactive species are present. This can be a particular problem if one is dealing with a biological fluid such as blood, serum or urine which can contain a very large number of reactive species. Clearly it would be desirable to have a method which could be used to separate the enzyme to be detected from other materials by a simple means, followed by a highly sensitive detection of the enzyme activity which could thus take place in the absence of interference by unwanted reactive species. Such a method has now been discovered.

Accordingly the present invention provides a method of detecting an enzyme in a liquid which method comprises (i) contacting the liquid with a support to which is attached a substance to which the enzyme will bind specifically without eliminating its enzymatic properties, so that said enzyme becomes associated with said support, (ii) separating the support with its associated enzyme from the liquid and (iii) using the support with its associated enzyme in an assay for the enzyme in which assay the enzyme associated with the support produces a modulator for a chemical reaction which causes a detectable change.

Techniques of this kind have not hitherto been worthy of development since in general assay methods for enzymes have not been suffiently sensitive to make such methods easy to apply. The use of enhanced assay methods disclosed herein and especially those of my U.S. Ser. No. 193,647 (which is incorporated herein by cross reference) are sufficiently sensitive to enable ready use of the new techniques disclosed herein.

The chemical reaction which causes a detectable change is aptly an enzymatic process which is caused to operate by the introduction of a modulator. Such systems are described hereinbefore.

The chemical reaction which causes a detectable change is aptly a cyclic chemical reaction. Such cyclic chemical reactions is most aptly an oxidation/reaction and will favourably employ a NAD/NADH or NADP/NADPH interconversion of which the NAD/NADH interconversion is preferred. This latter interconversion most desirably employs NAD as modulator in which case the enzyme most aptly detected is a phosphatase. Such a phosphatase may be an acid phosphatase or an alkaline phosphatase. Such cyclic reactions modulated by NAD are described in my compending unpublished UK Patent application No. 8104395 and herein and are particularly favoured examples of cofactor cycles.

The method of this invention is most suitably adapted to the detection of an enzyme in blood, serum or urine or, in extract, of tissues or microbiological extracts. Since enzymes are often used as markers in the diagnosis of human pathological conditions it follows that the method of this invention is preferably adapted to the detection of an enzyme in human blood, serum or urine. Of course use may be made of this invention in the vetinary field in analogous manner.

The support used in this invention may be in the form of a discrete surface such as that of a stick or dish or filter system or in the form of small particules such as a powder or in the form of gel materials. Aptly the support may be polystyrene, nylon, cross linked dextrans (such as Sephadex, Sepharose and Agarose), polyacrylamide, bromacetylcellulose or the like. Such materials are presently known for the immonobilization of non-enzymatic biological materials such as proteins, for example antigens, nucleic acids and the like. The skilled worker will appreciate that such supports can bind a wide range of materials so that, in conventional manner, in order to prevent uptake of unwanted enzymes or the like from the liquid the support will be neutralised to prevent this, for example by treatment with innocuous protein after the substance to which the enzyme to be detected is bound to the support.

The substance to be bound to the support will normally and preferably be an antibody to the enzyme with the proviso that the antibody employed will not be one that eliminates the enzymatic properties of the enzyme to be detected. Very desirably the antibody will be a monoclonal antibody.

The binding of the antibody (or other substance) to the support may be physical or chemical binding. Physical binding includes adsorption onto the surface of the support and chemical binding may be ionic or covalent. Sandwich systems are also envisaged. The antibody may be bound in any manner as long as it is still capable of specifically binding the enzyme in a manner which will not eliminate the enzyme activity.

Alternatively the substance to be bound to the support may be some other substance with specific affinity for the enzyme in question, such as a substrate, substrate-analogue or inhibitor substance for that enzyme. Such approaches are possible with enzymes having more than one active enzymatic site per enzyme molecule for—if only one site is taken up in binding to the support through the substrate, substrate analogue, inhibitor—the other site may still be available for catalytic activity.

Generally sufficient binding of the enzyme to the support with its bound substance will take place within 10 seconds to 30 minutes depending on the reaction parameters, concentrations employed and degree of accuracy required. More usually the binding will take place within 30 seconds to 10 minutes and preferably from 1 to 5 minutes. Mild agitation may be employed to facilitate the binding.

At the end of the binding stage the liquid may be separated and the support with the enzyme bound thereto washed. Generally it is preferred that this washing is thorough in order to remove unwanted unbound material. Washing may be carried out with water, saline, buffer or the like of which phosphate buffered saline is favoured. Suitably the washing liquid may include a mild surfactant such as a Tween.

At this point the support with the enzyme bound thereto may be promptly used in an assay for the enzyme.

As previously indicated that assay will aptly be one employing an amplification system such as that described in my earlier patent application hereinbefore identified.

Enzymes to be detected in this manner include kinases such as pyruvate kinase (especially type II) and creatin kinase and their various isoenzymes; phosphatases such as acid phosphatase and alkaline phosphatase and its various isoenzymes; dehydrogenases such as lactic dehydrogenase and its various isoenzymes; and the like.

Normally and preferably the assay employed will be adapted to produce a visually or spectrophotometrically determinable end point.

The following example illustrates the invention: Detection of alkaline phosphatase. Example A1.

The alkaline phosphatase used in this example is as obtainable from the Sigma Chemical Co (London) Ltd Type VII from bovine (calf) intestine catalogue number P4502 (1981). Antibody is raised against this material by any of the standard procedures. For example 0.5 mg of the alkaline phosphatase suspension is taken and made to 1.0 ml with distilled water and shaken gently. One ml of Freund's complete adjuvant is then added and the mixture homogenised through a connector between two hypodermic syringes back and forth until a stable water-in-oil emulsion is produced. Approximately 1 ml of the emulsion is then injected intramuscularly into each hindquarter of a rabbit. The injections are repeated two and four weeks later with the same amount of alkaline phosphatase but without the added Freund's adjuvant. Blood is then taken from the immunised animal two weeks after the last injection and the immuneserum taken off after clotting has taken place. An IgG fraction of the serum is then obtained by the standard procedure of DEAE Cellulose Chromatography set out in Methods in Immunology by D. H. Cambell, J. S. Garvey, N. E. Cremer and D. H. Sussdorf, 2nd Edition (1970) pages 193–197, published by W. A. Benjamin, Reading Mass. An aliquot of the IgG fraction is then diluted to a protein concentration of 0.5 mg/ml in 0.05M carbonate buffer at pH 9.6 and is used to coat the wells of polystyrene micro-haemagglutination trays (Type M29 AR Microtitre, Dynatech Laboratories) by the addition of 0.3 ml of diluted antiserum being added to each well and left either for 6–8 hours at room temperature or 1 hour at 37° C. The solutions are then taken out of the wells by suction and replaced with 0.2% lactalbium and left overnight. The wells are emptied and then washed three times with phosphate buffered saline containing 0.05% Tween 20 (PBS Tween). The plates are now ready for use.

Starting with a 1:1000 dilution, ten-fold dilutions of the original source of alkaline phosphatase were made down to 1:10$^7$ and 0.25 ml of each placed separately into the coated wells. The solutions are left for 30 minutes at room temperature (23° C.) and then removed by aspiration. The wells are again washed three times with PBS-Tween. The wells are then assayed for their alkaline phosphatase activity.

To each well is added 210 ul of 0.14M ethanolamine-HCl buffer at pH 9.3 and containing 5 mM $MgCl_2$ followed by 10 ul 10 mM thiazolyl blue (Sigm London Chemical Co), 10 ul of 40 mM phenazine ethosulphate (Sigma London Chemical Co), 5 ul of alcohol dehydrogenase especially free from NAD (Sigma London Chemical Co—catalogue number A3263) and 5 ul of 1M ethanol. Reactions are initiated by the addition of 10 ul of a 10 mM solution og NADP (Sigma London Chemical Co) to each well, the plate gently agitated and left at room temperature. The solutions in the wells to which a higher concentration of alkaline phosphatase was added show a change of colour from pale yellow to black much faster than did those which had been exposed to a lower concentration, indicating that the method not only detects the presence of alkaline phosphatase in the solution added to the wells but is also capable of quantification.

In a simple alternative, suitable (e.g. polystyrene) 1.0 ml plastic colourimeter cuvettes are coated with the IgG fraction of the antiserum as above. One ml samples of the alkaline phosphatase dilutions are then placed in individual cuvettes and incubated and washed as above. To each cuvette is then added 0.96 ml of 0.14M ethanolamine-HCl buffer at pH 9.3 and containing 5 mM $MgCl_2$ followed by 10 ul 10 mM thiazolyl blue, 10 ul 40 mM phenazine ethosulphate, 5 ul alcohol dehydrogenase (A3263) and 5 ul 1M ethanol. Reactions are initiated as before by the addition of 10 ul 10 mM NADP and the solutions mixed. The colour changes may then be monitored by eye or at 570 nm in a colourimeter for more precise quantification.

The general method is adaptable to the detection of other alkaline phosphatases including those from human origin, however, in each case it is usually advisable to prime the wells with a specific antiserum raised against the particular alkaline phosphatase in question. Furthermore, different alkaline phosphatases from human origin (such as from liver and bone) may be separately determined in a mixture of different types by means of IgG fractions directed specifically against particular types being used to charge specific wells.

This invention relates to a method of detecting a catalyst or a substrate in a catalysable reaction and to the use of this method in the detection of clinically or environmentally important materials present in trace amounts.

The desirability of having a method which can detect trace amounts of a catalyst or its substrate which is convenient and does not need the use of radioactive substances or complex equipment is obvious. Known methods of detection, for example heterogenous specific binding assays such as that of British Pat. No. 1548741 or homogenous specific binding assays such as that of British Pat. No. 1552607 are useful but can suffer from a lack of sensitivity. A particularly sensitive assay has now been discovered which does not require the use of radioactive substances or complex equipment.

Accordingly the present invention provides a method of detecting a catalyst or its substrate in a catalysable reaction which comprises carrying out an assay for the catalyst or the substrate in a manner which produces a product which method is characterized in that said product is an activator for an enzymatic reaction which is activated by the production thereof so as to effect a detectable change and to produce a facilitator for the enzymatic reaction; whereby said enzymatic reaction is enhanced.

When used herein the term "activator" means a substance which is required for an enzymatic reaction to take place if all other components needed for that enzymatic reaction are present.

When used herein the term "facilitator" means a substance which is not an enzyme but which acts so as to increase the rate at which the detectable change takes place. The facilitator is most suitably a cofactor for the enzymatic reaction.

Normally and preferably the facilitator produced by the enzymatic reaction is the same as the activator produced by the assay for the catalyst or its substrate. When the facilitator and activator are the same a desirable simplification of the system occurs. The feedback of the facilitator into the earlier part of the reaction sequence causes a marked increase in the rate of formation of the detectable change.

When used herein the term "detectable change" means a change in the concentration of a moiety which can be observed. The observation can be by any method but most aptly it is by a change is the optical characteristics. The change in the optical characteristics may be observed by eye or with the aid of a device such as a spectrophotometer. The change in concentration observed may be the increase in concentration of a moiety produced by the enzymatic reaction or it may be the decrease in concentration of a moiety consumed by the enzymatic reaction.

The enaymatic reaction may use a single enzyme or more than one enzyme. If more than one enzyme is employed it will aptly be not more than four enzymes, it will more aptly be not more than three and it will preferably be not more than two enzymes.

The catalyst to be detected may be an enzyme or a non-enzymic catalyst.

Normally and preferably the catalyst to be detected is an enzyme. Enzymes are often required to be detected in clinical chemical or vetinary investigations. Abnormal levels of enzymes can be present in pathological conditions so that their detection (either qualitatively or quantitatively) can be used as a diagnostic aid or to monitor the progress of the pathological state. Thus, for example, it is desirable to detect such enzymes as kinases, for example creatine kinase (a marker for breast cancer and of use in diagnosing myocardial infarction and brain damage and the like) and pyruvate kinase (for diagnosis and monitoring of liver & muscle pathology; and dehydrogenases, for example lactodehydrogenase (for diagnosing blood diseases and liver diseases); and the like.

Alternatively the catalyst may be a non-enzymatic catalyst such as an electron transfer reagent. The electron transfer reagent can be a molecule such as phenazine ethosulphate or its analogues or a quinone or the like and may be conjugated to another molecule if desired.

If the method of this invention is used to detect a substrate for a catalyst it is normally and preferably a substrate for an enzyme. Such materials can have clinical significance, for example pyridine nucleotides such as ATP, GTP, CTP, UTP and the like or creatine phosphate or the like. Such materials are often of interest in metabolic studies and studies of kidney function.

Naturally, the terms "activator" and "facilitator" used herein cannot be interpreted as interconverting substances as in conventional cycles such as those of British Pat. Nos. 1,548,741 and 1,552,607.

The preferred enzymatic reaction for use in the amplification method of this invention comprise kinases or dehydrogenases.

A particularly apt enzymatic reaction employing kinases may be represented as follows:

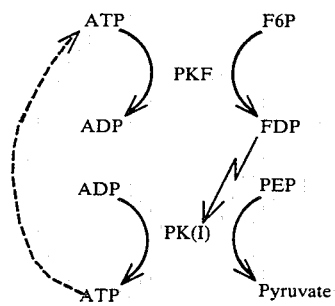

In this system the production of ATP (produced by the assay and hence the "activator") enables the PKF to convert F6P to FDP. The thus produced FDP activates the PK(I) which converts the ADP present to ATP and the PEP to pyruvate (which causes a detectable change as explained hereinafter). The ATP produced by the PK(I) (the "facilitator") feeds back to allow the PFK to produce more FDP which increases the activity of the PK(I) which leads to the production of more ATP and pyruvate. Hence a marked increase in production of pyruvate occurs which in turn leads to a marked increase in the rate of detectable change.

An apt method of using the above enzymatic reaction to lead to a detectable change is to employ the following system:

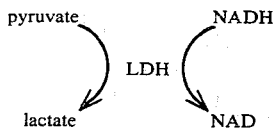

In this system the introduction of pyruvate causes the LDH to oxidize the NADH to NAD. This can then be monitored spectrophotometrically, for example at 340 nm.

It will be appreciated that the preceeding enzymatic reaction can be adapted to the detection of a nucleotide triphosphate such as ATP or an enzyme that produces such a triphosphate or even a substrate for such an enzyme. Most desirably the preceeding enzymatic reaction is adapted to the detection of an enzyme which produces ATP. The preferred ATP producing enzymes are kinases which do not require FDP for their activation. Such enzymes include pyruvate kinase (PKII) and creatine kinase (CK) (sometimes also called creatine phosphokinase).

In the case of (PK II) a reaction leading to the production of the activator (ATP) is as follows:

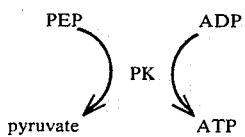

In the case of CK a reaction leading to the production of the activator (ATP) is as follows:

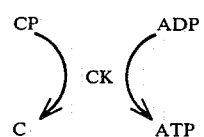

A particularly apt enzymatic reaction employing dehydrogenase may be represented as follows:

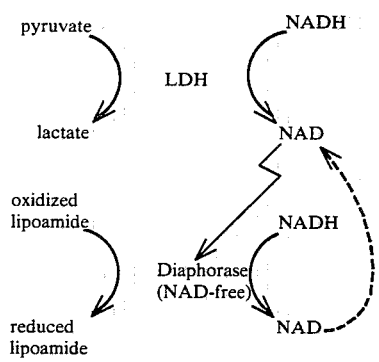

Diaphorase resins NAD to function so that NAD-free diaphorase is activated by the NAD produced by the catalyst (in the shown scheme the catalyst is LDH).

The detectable change produced by this reaction is the production of NAD from NADH which may be monitored at 340 nm.

The skilled worker will appreciate that the reactions hereinbefore discussed are biochemical reactions of the type that will be performed under substantially physiological conditions; that is in aqueous solution under non-extreme conditions, for example at a temperature of 5°–40° C. and more usually 15°–37° C.; at pH values of 5–9, more usually of 5.5–8.5 and preferably at approximately 7 (pH will generally be maintained in the desired range using a buffer such as DMG or imidazol buffer).

It is envisaged that normally all the reagents required for operation of the assay and enzymatic reactions will be present except the activator, facilitator and the material to be detected. The method of this operation comes into effect when the material to be detected is added.

With respect to this form of the invention [detecting the catalyst or its substrate], the term "detecting" extends to quantitative as well as non-quantitative methods; this is often referred to as "determining".

In a broad aspect this invention provides a method of detecting an activator (as hereinbefore defined) which comprises contacting said activator with an enzyme to be activated and all other components needed for the enzymic reaction to proceed characterized in that said enzymatic reaction causes a detectable change and the production of a facilitator (as hereinbefore defined) (whereby said enzymatic reaction is enhanced).

The activator may be a substrate for an enzyme or it may not be a substrate for an enzyme in which case it will usually be an effector or other substance which can cause the enzyme to operate.

The facilitator may be produced as a direct product of the enzymatic reaction or may be produced as a product of a further reaction initiated by the direct product of the enzymatic reaction.

The facilitator produced by the enzymatic reaction is desirably the same as the activator so that a simple system results.

In one favoured form the activator and facilitator are both ATP

An alternative favoured system employs an activator which is a derivative of the facilitator. In such systems the activator is envisaged as a ligand or receptor labelled with the facilitator. In this aspect the skilled worker will appreciate that this aspect of the invention also provides a method of detecting said ligand or receptor labelled with facilitator. Preferably the ligand or receptor labelled in this way is an antigen or antibody (when used herein the term "labelled" means chemically or physically associated in a manner which will not prevent the activation of the enzyme by the thus formed activator).

In yet another system the activator is different from the facilitator and is not a ligand or receptor labelled with a facilitator.

Favoured facilitators for use in this invention include pyridine nucleotides and ligands or receptors labelled with a pyridine nucleotide, preferred facilitator pyridine nucleotides include ATP and NAD. Preferred ligands and receptors labelled with a pyridine nucleotide include antigens and antibodies labelled with ATP or NAD. British Pat. Nos. 1548741 and 1552607 disclose ligands or receptors labelled with pyridine nucleotides which may be employed as activators in this invention (however said patents did not disclose the use of a system in which amplification was achieved by use of a facilitator which fed back into the assay).

A favoured example of a method of detecting an activator according to this invention is the detection of NAD or a ligand or receptor labelled with NAD which comprises contacting said activator with NAD-depleted diaphorase, NADH and other required substrate (such as oxidized lipoamide or oxidized lipoic acid) characterized in that said reaction causes a detectable change (the removal of NADH) and the production of a facilitator (NAD).

A favoured example of a method of detecting an activator according to this invention is the detection of ATP or a ligand or receptor labelled with ATP which comprises contacting said activator with PFK, F6P, PK(I), ADP, PEP whereby F6P is converted by PFK to FDP which causes PK(I) to convert ADP to ATP and PEP to pyruvate which ATP is the facilitator and which conversion of PEP to pyruvate is the detectable change.

(The conversion of PEP to pyruvate can be detected by a method as hereinbefore described, for example by reaction with a hydrazine or by a further enzymatic change).

The direct product of the preceeding activated enzyme is FDP. The thus produced FDP then triggers the PK(I) to produce a detectable change.

A particularly simple way of carrying out the method of this invention is to have the above reagents in an appropriate cuvette of a spectrophotometer and to add the solution possibly containing the material to be detected. If the material to be detected is not present no change occurs but if it is present the change may be observed.

If desired the use of a spectrophotometer can be obviated in systems producing pyruvate (such as the kinase systems hereinbefore described) by detecting the formation of the reaction product between pyruvate and a hydrazine such as 2,4-dinitrophenylhydrazine which gives rise to a visually (or machine) detectable coloured product when the pH is subsequently rendered alkaline (for example with sodium hydroxide solution).

As previously explained, the method of this invention is usefully employed in investigating enzymes in biological samples. Unfortunately biological fluids, such as blood, serum and urine can contain a number of reactive species. Clearly it would be desirable to adapt the method of this invention to work with small samples of fluid possibly containing only small amounts of enzymes. Although this will employ a purification step, the increased sensitivity of this method is such as to render losses during purification acceptable.

Accordingly in a further aspect this invention provides a method of detecting an enzyme in a liquid which method comprises (i) contacting the liquid with a support to which is attached a substance to which the enzyme will bind specifically without eliminating its enzymatic properties, so that said enzyme becomes associated with said support, (ii) separating the support with its associated enzyme from the liquid and (iii) using the support with its associated enzyme in a detection method of this invention as hereinbefore described.

This aspect of the invention is most suitably adapted to the detection of an enzyme in blood, serum, urine, tissue extract or microbiological extract. Since enzymes are often used as markers in the diagnosis of human pathological conditions it follows that the method of this invention is preferably adapted to the detection of an enzyme in human blood, serum or urine. Of course use may be made of this invention in the vetinary field in analogous manner.

The support used in this invention may be in the form of a discrete surface such as that of a stick or dish or filter system or in the form of small particles such as a powder or in the form of gel materials. Aptly the support may be polystyrene, nylon, cross linked dextrans (such as Sephadex, and Sepharose) Agarose, polyacrylamide, bromoacetylcellulose or the like. Such materials are presently known for the immobilization of non-enzymatic biological materials such as proteins, for example antigens, nucleic acids and the like. The skilled worker will appreciate that such supports can bind a wide range of materials so that, in conventional manner, in order to prevent uptake of unwanted enzymes or the like from the liquid the support will be neutralised to prevent this, for example by treatment with innocuous protein after the substance to which the enzyme to be detected is bound to the support.

The substance bound to the support will normally and preferably be an antibody to the enzyme with the proviso that the antibody employed will not be one that eliminates the enzymatic properties of the enzyme to be detected. Very desirably the antibody will be a monoclonal antibody.

The binding of the antibody (or other substance) to the support may be physical or chemical binding. Physical binding includes absorption onto the surface of the support and chemical binding may be ionic or covalent. Sandwich systems are also envisaged. The antibody may be bound in any manner as long as it is still capable of specifically binding the enzyme in a manner which will not eliminate the enzyme activity.

Alternatively the substance to be bound to the support may be some other substance with specific affinity for the enzyme in question, such as a substrate, substrate-analogue or inhibitor substance for that enzyme. Such approaches are possible with enzymes having more than one active enzymic site per enzyme molecule for—if only one site is taken up in binding to the support through the substrate, substrate analogue, inhibitor—the other site may still be available for catalytic activity.

Generally sufficient binding of the enzyme to the support with its bound substance will take place within 10 seconds to 30 minutes depending on the reaction parameters, concentrations employed and degree of accuracy required. More usually the binding will take place within 30 seconds to 10 minutes and preferably from 1 to 5 minutes. Mild agitation may be employed to facilitate the binding.

At the end of the binding stage the liquid may be separated and the support with the enzyme bound thereto washed. Generally it is preferred that this washing is thorough in order to remove unwanted unbound material. Washing may be carried out with water, saline, buffer or the like of which phosphate buffered saline is favoured. Suitably the washing liquid may include a mild surfactant such as a Tween.

At this point the support with the enzyme bound thereto may be promptly used in an assay for the enzyme.

In another and important aspect this invention provides a diagnostic test which comprises carrying out a method of this invention as hereinbefore described on a biological fluid or on material obtained from a biological fluid as hereinbefore described.

Desirably this aspect of the invention comprises a diagnostic test for breast cancer employing creating kinase as hereinbefore described.

Aptly this aspect of the invention comprises a diagnostic test for muscle damage and also for liver disease employing pyruvate kinase as hereinbefore described.

In this specification the following symbols and abbreviations have the following meanings:

⇀ indicates activation of an enzyme.
----▶ indicates a feed-back of facilitator into the reaction sequence.
AMP: adenosine 5'-monophosphate
ADP: adenosine 5'-diphosphate
ATP: adenosine 5'-triphosphate
GTP: guanosine 5'-triphosphate
CTP: cytidine 5'-triphosphate
UTP: uridine 5'-triphosphate
F6P: fructose-6-phosphate
FDP: fructose-1,6-diphosphate
PEP: phospho(enol)pyruvate
Pyr: pyruvate
CP: creatine phosphate
C: creatine
NAD: nicotinamide adenine dinucleotide
NADH: reduced nicotinamide adenine dinucleotide
NAC: N-acetyl cysteine
LDH: lactic deihydrogenase
PFK: phosphofructokinase
CK: creatine kinase
PK: pyruvate kinase
PK(I): pyruvate kinase activatable by FDP§
PK(II): pyruvate kinase not activatable by FDP§
EDTA: ethylenediaminetetraacetic acid
DMG: dimethyl-glutamate §as described by M. Malcovati, G. Valentini, & H. L. Kornberg in Acta vitamin. enzymol. (Milano) 1973, 27, 96.

The following examples illustrate the invention. The following description illustrates the preparation of useful reagents.

DEMONSTRATION

Preparation of Pyruvate Kinase (I) for the Examples

Cultures of *E. coli* strain K1-1 were grown on a synthetic medium containing essential nutrients and glycerol as carbon source, until well into their logarithmic phase of growth. The cells were harvested, washed by centrifugation and resuspended in a sonication buffer of 5 mM phosphate, 1 mM EDTA, 2 mM mercaptoethanol pH 7.5 in an amount of approximately 20 mg dry weight per ml. They were then disrupted with an MSE ultrasonic disintegrator for 4 minutes (in 30 second bursts while cooled). The resulting crude extract was separated from cell debris by centrifugation. As well as containing pyruvate kinase (I) this extract also contained an interfering isoenzyme with different properties, and also a number of other interfering enzyme activities. It was found, however, that it was possible to remove these contaminants by heating the extract to 55° C. for 20–60 for example 45 minutes. This is the source of pyruvate kinase (I) referred to in the following examples.

EXAMPLE B1

Detection of Pyruvate kinase (II)

In order to demonstrate the enhancement in sensitivity brought about by the method of this invention an assay for pyruvate kinase (II) was carried out with and without a secondary system to produce amplification. The two assays may be represented as follows:

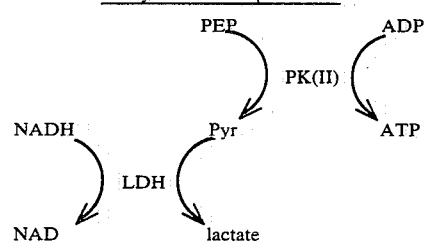

Assay without Amplification

Assay with amplification

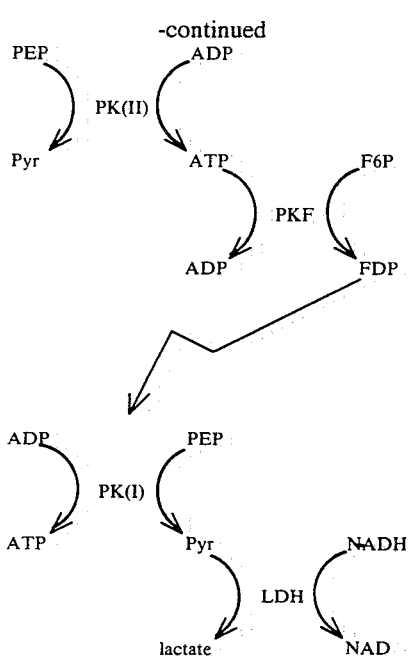

As PK(I) can in the absence of FDP be activated by a high enough concentration of PEP, it is necessary to limit the PEP concentrations used to those which will not cause spontaneous activation, while maintaining a sufficient substrate concentration for the enzyme. A concentration of 1 mM has been found to satisfy these requirements under the conditions employed so far.

In the assay system without amplification PK(II) converts PEP and ADP into pyruvate and NADH to NAD and lactate. The change in concentration of NADH can be monitored by absorbence at 340 nm.

In the assay system with amplification (that is the assay incorporating the secondary system) the preceeding sequence takes place but in addition the secondary system generates ATP. In this amplified system, in addition to the PEP, ADP, NADH, PK(II) and LDH present in the nonamplified system, the following are also present: F6P, PFK and PK(I). In the presence of ATP (generated by catalyst PK(II)) the PFK converts the F6P into FDP. The FDP activates the PK(I) which then is available to convert the PEP and ADP to ATP and pyruvate. The ATP thus produced feeds back within the secondary system and the pyruvate is converted into lactate by LDH in the presence of NADH. This end reaction is monitored at 340 nm as in the unamplified assay.

To indicate the usefulness of this amplification method the PK(II) was initially assayed by the direct reaction as follows: The assay mix was as shown in Table 6 (left column) with a buffer consisting of 10 mM dimethylglutamate (DMG) pH 6.8 5 mM MgCl$_2$. All assays were carried out at 30° C. The PK(II) was obtained from Calbiochem and, as a result of trials, a standard amount chosen which gave the activity shown in the Table. This amount was used for all following experiments. PK(I) was as in previous experiments.

The assay system including the positive feed-back amplifier was composed as shown on the right hand column of Table 6. The activity attributable to the addition of the same amount of PK(II) as before and after allowing the feedback system to get underway for seven minutes, is shown. The activity attributable to PK(II) is raised eleven times over the direct method.

TABLE 6

|  | Direct assay | Feed-back assay |
|---|---|---|
| ADP | 0.4 mM | 0.4 mM |
| PEP | 1.0 mM | 1.0 mM |
| NADH | 0.1 mM | 0.1 mM |
| LDH | 1.1 U | 1.1 U |
| PK(II) | standard | standard |
| F6P |  | 2.0 mM |
| PFK |  | 1.0 U |
| PK(I) |  | 10 μl |
| Buffer | To 1.0 ml | To 1.0 ml |
| Rate of Change Absorbence (OD Units at 340 nm per 10 minutes) | 0.005 | 0.055 |

Using the direct method, the standard amount of PK(II) could just about be detected whereas it was quite readily detectable using the feed-back amplifier.

EXAMPLE B2

Detection of ATP

In this example the same basic system described in Example 1 was again used, but instead of the system being used to detect an enzyme capable of giving rise to ATP, the pre-existing ATP in a solution was assayed, using a PK(I) extract which had been prepared by heating at 55° C. for 60 minutes.

As in the previous example, the assays were carried out in quartz spectrophotometer cuvettes for use with 1.0 ml assay mixtures. They were made to contain:
ADP: 0.4 mM
PEP: 1.0 mM
NADH: 0.1 mM
LDH: 1.1U
F6P: 2.0 mM
PK(I): 10 ul
PFK: 1.0U
material to be assayed
buffer: to 1 ml All dilutions and solutions were made in this same buffer. The buffer was 10 mM dimethyl-glutarate pH 6.8 and containing 5 mM MgCl$_2$.

The test solutions were made to give a final ATP concentration in the cuvette of: 0.4 mM; 0.05 mM; 0.01 mM; 0.001 mM; 0.0001 mM; control—with no ATP. On addition of a sample to the cuvette containing the above components the contents were mixed and the oxidation of NADH followed at 340 nm and 30° C. with a spectrophotometer. The higher concentrations of ATP gave rise to an earlier initiation of observable NADH oxidation and subsequently increased in their rate faster than the lower concentrations. The method therefore has utility both in showing the presence of very low concentrations of ATP and also in demonstrating concentration.

EXAMPLE B3

Detection of Creatine Kinase

The basis for this example is the same as that for with pyruvate kinase described in Example 1. Using the same system creatine kinase can be detected in the presence of its substrate creatine phosphate as then the creatine kinase gives rise to ATP from the ADP present and this activates the system as described in the previous example. The assay conditions themselves are in part based upon those described in Methods in Enzymatic analysis pages 789–793, edited by Hans Ulrich Bergmeyer and published by Verlag Chemie Gmbh, Weinheim, 1974.

For determination of creatine kinase a quartz cuvette for use with 1.0 ml assay mixtures is made to contain a solution of the following composition:
ADP: 0.4 mM
PEP: 1.0 mM
NADH: 0.1 mM
LDH: 1.1U
F6P: 2.0 mM
PFK: 1.0U
PK(I): 10 ul
MgCl$_2$: 10 mM
CP: 5 mM
CK: material assayed The mixture is combined in DMG buffer to a final volume of 1.0 ml, pH 6.8 and a DMG concentration of 25 mM. On addition of the material to be assayed the contents of the cuvette are mixed and the oxidation of NADH followed spectrophotometrically at 340 nm and 30° C. as before. Ten-fold dilutions of creatine kinases (creatine phosphokinases) obtained from the Sigma London Chemical Company (Type I from rabbit muscle, C3755, Type III from bovine heart, C7886 and Type IV from rabbit brain, C6638) are made to provide final concentration of from 1U to 0.001U in the assay mixture when added. Creatine kinase specific activation of the system leads to NADH oxidation, in an analogous manner to the previous example and is dependent on CK concentration.

EXAMPLE B4

Detection of Creatine Kinase

Example 3 may be repeated including 10 mM of NAC. (This acts as an thiolic activating agent for the enzyme and aids in increasing the sensitivity of the system.)

EXAMPLE B5

Detection of Creatine Kinase in Suspected Presence of Myokinase

Myokinase is sometimes a minor contaminent of enzymes such as PK(I). In order to allow the assay of examples 3 or 4 to take place in the presence of trace amounts of myokinase a sufficiency of AMP (for example 10 mM) may be employed in the assay. (Inclusion of AMP in assays involving biological fluids is similarly desirable for this reason).

EXAMPLE B6

Five hundred units of creatine phosphokinase from bovine heart and obtained from the Sigma (London) Chemical Company Ltd (Type III catalogue number C7886) was dissolved in 1 ml of the standard buffer used in the assay—namely: 10 mM dimethyl-glutarate buffer at pH 6.8 and containing 5 mM MgCl$_2$ and 0.1% in bovine serum albumin (Sigma London catalogue number A6003). Three ten-fold serial dilutions of this enzyme solution were then made using the same buffer. Ten micro-liter aliquots of each of the dilutions were then tested in standard mixtures of the following composition for their ability to form ATP and thus activate the system.
ADP: 0.4 mM
PEP: 1.0 mM
NADH: 0.1 mM
F6P: 2.0 mM
CP: 4.0 mM
LDH: 1 enzyme unit
PFK: 1 enzyme unit
PK(I): 10 ul standard preparation The LDH was obtained from The Boehringer Corporation (London) Ltd—Cat. No. 127884 (from rabbit muscle). All other components except the standard PK(I), which was prepared as previously described, were obtained from the Sigma (London) Chemical Company and were as follows: ADP Grade 1 Cat. No. A 0127; PEP monopotassium salt Cat. No. P7127; NADH dipotassium salt Cat. No. N 4505; F6P disodium salt Grade 1 Cat. No. F 3627; CP disodium salt hydrate Cat. No. P 6502; PFK Type III from rabbit muscle Cat. No. F 6877.

The complete assay mixture for each test was made to 1 ml with the standard buffer in a suitable quartz spectrophotometer cuvette at 30° C. On addition of the final component (the creatine phosphokinase to be assayed) the contents of the cuvette were well mixed and the oxidation of NADH followed by continuous monitoring at 340 nm. The rate of change in optical density at two minutes after initiation was taken for each test and used to compare the activities as follows:

| Units of CK in final assay mixture | O.D. Units (340 nm) change/minute at 2 minutes |
|---|---|
| 0.05 | 0.0216 |
| 0.005 | 0.0068 |
| nil | 0.0017 |

Enzyme Units where quoted in the text are those units used by the particular manufacturers for the enzymes they have supplied.

EXAMPLE B7

This example uses the same reagents and conditions as Example 6, however, instead of showing the dependence of the system on the enzyme creatine kinase in the presence of its substrate creatine phosphate it shows that the system can be made dependent on the presence of the substrate creatine phosphate if creatine kinase is present as a reagent.

Mixtures were made up in 10 mM dimethyl-glutamate buffer at pH 6.8 and containing 5 mM MgCl$_2$ and 0.1% in bovine serum albumin as follows:

| | | | |
|---|---|---|---|
| ADP | 0.4 mM | 0.4 mM | 0.4 mM |
| PEP | 1.0 mM | 1.0 mM | 1.0 mM |
| NADH | 0.1 mM | 0.1 mM | 0.1 mM |
| F6P | 2.0 mM | 2.0 mM | 2.0 mM |
| LDH | 1 U | 1 U | 1 U |
| PFK | 1 U | 1 U | 1 U |
| PK(I) | 10 μl | 10 μl | 10 μl |
| CK | 0.05 U | 0.05 U | 0.05 U |
| CP | 4.0 mM | 0.04 mM | nil |

In each case the components were combined from stock solutions in a quartz cuvette of 1 ml capacity, mixed and immediately monitored for NADH oxidation by following their optical density at 340 nm and 30° C. The rate of change of absorbance at 1.5 minutes after mixing was found to be as follows:

| CP concentration | O.D. Units (340 nm) change/minute at 1.5 minutes |
| --- | --- |
| 4.0 mM | 0.0118 |
| 0.4 mM | 0.0070 |
| nil | 0.0011 |

The system was seen to be dependent on the presence of creatine phosphate and the concentration thereof.

This invention relates to chemical compositions and their use in enhancing assays.

In my European Patient Application No. 803034784 I disclose inter alia how a ligand or receptor could be determined by carrying out an assay requiring a conjugate between the ligand or receptor and a primary enzyme which was capable of producing a modulator for a secondary system, allowing the primary system to produce the modulator and allowing the secondary system to function in the presence of the modulator and determining a product of that secondary system. In my later as yet unpublished British Patent Application No. 8107249 (incorporated herein by cross reference) I further described the effectiveness of cycling the coenzymes NAD and NADH and the desirability of initiating the coenzyme cycle by producing NAD by the action of a phosphatase conjugate upon NADP.

It has now been discovered that a simple mixture of chemical may be employed to adapt conventional systems for determining a ligand or its substrate employing a phosphatase conjugate which produces NAD which adaption can be used to produce a more conveniently detectable change.

The present invention provides a chemical composition comprising (i) NADP, (ii) an enzyme capable of oxidising a substrate to product in the presence of NAD as coenzyme for the enzyme, (iii) a substrate for said enzyme, (iv) thiazolyl blue and (v) an electron transfer reagent for thiazolyl blue.

When employed in determining a ligand or receptor these reagents take part in the following system:

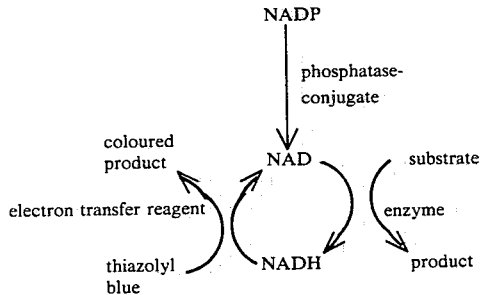

The enzyme employed may favourably be alcohol dehydrogenase (hereafter ADH), lactate dehydrogenase (hereafter LDH) or other similar enzymes which require selectively NAD and not NADP as cofactor such as formate dehydrogenase, acetaldehyde dehydrogenase, glyoxylate dehydrogenase, D-glycerate dehydrogenase, L-malate dehydrogenase, dihydro-orotate dehydrogenase, cytochrome $b_5$ reductase, hydrogen dehydrogenase, alpha-glycerophosphate dehydrogenase, triosephosphate dehydrogenase, glucose dehydrogenase, dihydrolipoate dehydrogenase, glutathione reductase, L-$\beta$-hydroxybutyryl CoA dehdrogenase, UDPG dehydrogenase, $\beta$-hydroxysteroid dehydrogenase, 3-$\alpha$-hydroxysteroid dehydrogenase, cytochrome c reductase.

The substrate for ADH will be an alcohol such as ethanol. The substrate for LDH will be lactic acid or more conventionally a salt thereof such as its sodium salt. The substrate for formate dehydrogenase will be formic acid or more conventionally salt thereof. The substrate for acetaldehyde dehydrogenase will be acetaldehyde. The substrate for glyoxylate dehydrogenase will be glyoxylic acid or more conventionally a salt thereof. The substrate for D-glycerate dehydrogenase will be D-glyceric acid or more conventionally a salt thereof. The substrate for L-malate dehydrogenase will be L-malic acid or more conventionally a salt thereof. The substrate for dihydro-orotate dehydrogenase will be dihydro-orotic acid or more conventionally a salt thereof. The substrate for cytochrome $b_5$ reductase will be cytochrome $b_5$ in its reduced form. The substrate for hydrogen dehydrogenase will be hydrogen. The substrate for $\alpha$-glycerophosphate dehydrogenase will be $\alpha$-glycerophosphate. The substrate for triosephosphate dehydrogenase will be triosephosphate. The substrate for D-glucose dehydrogenase will be D-glucose. The substrate for dihydrolipoate dehydrogenase will be lipoamide, lipoic acid or more conventionally a salt thereof. The substrate of glutathione reductase will be glutathione in its reduced form. The substrate for L-$\beta$-hydroxybutyryl CoA dehydrogenase will be L-$\beta$-hydroxybutyryl CoA. The substrate for UDPG dehydrogenase will be uridine-5'-diphosphoglucuronic acid or more conventionally a salt thereof. The substrate of $\beta$-hydroxysteroid dehydrogenase will by a $\beta$-hydroxysteroid. The substrate of 3-$\alpha$-hydroxysteroid dehydrogenase will be a 3-$\alpha$-hydroxysteroid. The substrate of 17-$\beta$-hydroxysteroid dehydrogenase will be a 17-$\beta$-hydroxysteroid. The substrate for cytochrome c reductase will be cytochrome c in its reduced form.

The electron transfer reagent is most suitably phenazine ethosulphate (hereafter PES) which aids in the production of the colour change which occurs on the reduction of thiazolyl blue (hereafter MTT) (also called 3-(3,4-dimethylthiazolyl-2-)-2,5-diphenyl tetrazolium) when a yellow colour is converted to a dark colour (a blueish/greyish/blackish colour). This colour change may be detected visually and quantification can be achieved by comparison to standards or by measurement with a colourimeter set to 570 nm.

The composition of this invention will desirably also contain (vi) a buffer. The buffer will be chosen so that the system operates under favourable conditions of pH. If the phosphatase-conjugate employed is a conjugate of alkaline phosphatase the buffer employed to maintain the coenzyme cycle will suitably be one which also allows the alkaline phosphatase to operate, for example pH 8–10.5, more aptly 8.7–9.5 for example 9.3). If the phosphatase-conjugate employed is a conjugate of acid phosphatase then it may be that the coenzyme cycle does not work efficiently at the pH required for the initial reaction (generally pH 4–7, for example 5.6). Under such circumstances the initial reaction is allowed to take place at such acid pH and the coenzyme cycle subsequently takes place buffered to the preceding alkaline pH values.

Suitable buffers for maintaining alkaline pH values include: sodium 5:5-diethylbarbiturate-HCl; Tris(hydroxymethyl)aminomethane; 2-amino-2-methyl1:3-propanediol-HCl; ethanolamine-HCl; diethanolamine-HCl; boarate-HCl; glycine-NaOH.

Suitable buffers for maintaining acid pH values include: citric acid-Na$_2$HPO$_4$; citric acid-sodium citrate; $\beta$:$\beta'$-dimethylglutaric acid-NaOH; sodium acetate-acetic acid; succinic acid-NaOH; sodium cacodylate-HCl; sodium hydrogen maleate-NaOH.

The compositions of this invention most suitably are provided in the form of a single formulation such as a tablet, powder within a sachet, bottle, or sealed tube or the like. Alternatively the composition of this invention may be provided in two or more part fomulation within a single package when some of the components of the composition are in one part (such as a tablet, powder or the like) and the other components are in one or more other parts (such as another tablet, powder or the like or solution within a bottle or the like). Normally multi-part formulations do not contain more than four parts more sutiably not more than three parts and preferably not more than two parts. Mutli-part formulations are envisaged as of use when a liquid component is required to be contained separate from solid components or when better stabilities can be achieved by maintaining the components separate.

The solid forms of this invention may be prepared by conventional methods of mixing and tabletting (preferably, under dry conditions) and conventional excipients may be employed in conventional manner as long as they are chosen to avoid interfering with the assay. Similarly solutions may be prepared by dissolving the materials in deionised or distilled water and filled into containers.

The compositions of this invention also aptly contain a source of magnesium ions such as magnesium chloride.

Solid forms of this invention may be wrapped in water-proof wrappings such as foils or the like.

Multidose forms will be packaged together in conventional manner, for example in a box, carton, pouch, envelope or the like or are wrapped with film or the like.

Normally the compositions are provided with a light proof package.

The compositions of this invention will normally be accompanied by instructions for use.

Also within the scope of this invention is a chemical composition hereinbefore described containing alcohol dehydrogenase as the enzyme except in this aspect the composition does not contain ethanol which may be subsequently added from another source.

In a favoured aspect this invention provides an aqueous solution of components (i), (ii), (iii), (iv) and (v) of the chemical composition hereinbefore set forth.

Most aptly the aqueous solution of this invention will also contain buffers to maintain its pH to the conditions as set forth hereinbefore.

In use the aqueous solution containing the components of the chemical composition is contacted with phosphatase-conjugate being determined (which may be in solution or on a surface). The solution is then left until a colour develops or for a predetermined time, for example 1-60 minutes or more conventionally 20 minutes.

The compositions of this invention will contain the components in amounts such that a suitable colour change occurs when tested against standard samples of the phosphatase-conjugate.

The following examples illustrate the invention.

EXAMPLE 1

A Composition Suitable for Enhancing Alkaline Phosphatase-Conjugate Dependent Assay a. A solution is prepared of 100 ml consisting of 0.1M ethanolamine-HCl with 5 mM MgCl$_2$ and 0.1M ethanol at pH 9.3. The solution is placed in a brown glass 120 ml bottle which is then closed.

b. A mixture of the following:
thiazolyly blue: 4.1 mg
phenazine ethosulphate 1.7 mg
NADP: 7.6 mg
alcohol dehydrogenase: 2.4 mg (of Sigma Chemical Company catalogue number A3263≡780 units of enzyme).

The materials in powder form are placed in a foil sachet which is sealed.

c. The bottle and sachet are placed in a foil pouch which is sealed.

For use the pouch is opened and the bottle and sachet removed. The sachet and bottle are opened and the added to the liquid in the bottle and allowed to dissolve. The resulting solution is suitable for use to enhance an assay requiring an alkaline phosphatase conjugate. It is preferably used immediately. Less desirably it may be stored in its closed dark brown bottle for a few hours at 0°-4° C.

The 100 ml of solution is sufficient for 100 1 ml tests.

EXAMPLE 2

A Composition Suitable for Enhancing Alkaline Phosphatase-Conjugate Dependent Assay This is provided as in Example 1 but with the alcohol dehydrogenase packaged separate from the other solids. In use the other solids are first added to the liquid and the alcohol dehydrogenase added subsequently just before the assay is conducted.

EXAMPLE 3

A Composition Suitable for Enhancing Acid Phosphatase-Conjugate Dependent Assay a. A solution is prepared of 25 ml consisting of 20 mM citric acid-sodium citrate at pH 5.6. The solution is placed in a brown 30 ml bottle which is then closed.

b. Solid:
NADP: 7.6 mg
This is placed in a foil sachet which is sealed.

c. A solution is prepared of 75 ml consisting of 0.14M ethanolamine-HCl and 0.1M ethanol at pH 9.3. The solution is placed in a brown 80 ml bottle which is then closed.

d. A mixture of the following:
thiazolyl blue: 4.1 mg
phenazine ethosulphate: 1.7 mg
alcohol dehydrogenase: 2.4 mg (Sigma A3263)

The materials in powder form are placed in a foil sachet which is sealed.

e. The bottles and sachets are placed in a foil pouch which is sealed.

For use the pouch is opened and the bottles and sachets removed. Solid (b) is added to solution (a) and allowed to dissolve. Mixture (d) is added to solution (c) and allowed to dissolve. The resulting solutions allow enhancement of an assay requiring an acid phosphatase-conjugate. One volume of the solution made from (b)+(a) is first added to the substance possible containing the conjugate. If the substance be liquid its pH must have previously been adjusted to 5.6. After a set time such as ten minutes at a moderate temperature such as 30° C. with gentle agitation (especially if the acid-phosphatase be solid bound) four volumes of the solution made from (d)+(c) is mixed in and the incubation continued as above for a set time such as ten minutes or until a particular colour change is evident.

The solutions described above for packaging and storing may be rendered sterile and stored in this form to increase their stability. For example a bacteriocidal concentration of sodium azide (such as 0.05%) may be added.

What I claim is:

1. In an immunoassay in which a conjugate of a phosphatase is contacted with a phosphate of an organic compound which is thereby dephosphorylated causing a determinable change which is determined, the improvement which comprises employing as the phosphate of the organic compound a phosphate of a nicotinamide adenine dinucleotide whereby a nicotinamide adenine dinucleotide is produced by the conjugate of a phosphatase which is contacted with the components of a cyclic chemical reaction which is activated by the nicotinamide adenine dinucleotide, which cyclic chemical reaction interconverts said nicotinamide adenine dinucleotide and its reduced form and thereby regenerates said nicotinamide adenine dinucleotide and produces a determinable change, said components of the cyclic chemical reaction being present in sufficient quantity to maintain the cyclic chemical reaction and produce determinable change as the cyclic chemical reaction proceeds, whereby amplification occurs.

2. The improvement according to claim 1 in which the immunoassay is an enzyme linked immunoabsorbent assay in which the determinable change results from the production of a determinable product.

3. The improvement according to claim 2 which employs a monoclonal antibody.

4. The improvement according to claim 3 wherein the conjugate comprises a monoclonal antibody.

5. The improvement according to claim 1 in which the determinable change results from the production of a determinable product.

6. The improvement according to claim 1 wherein the conjugate is a conjugate of an alkaline phosphatase.

7. The improvement according to claim 1 wherein NADP is converted to NAD by the conjugate and the NAD starts a cyclic chemical reaction which proceeds at pH 8–10.5 to interconvert NAD and NADH.

8. The improvement according to claim 7 in which the reduction of NAD to NADH is effected by a dehydrogenase.

9. The improvement according to claim 8 wherein the reductase is an alcohol dehydrogenase.

10. The improvement according to claim 9 wherein the oxidation of NADH to NAD accompanies reduction of a tetrazolium compound whereby a colour change is produced.

11. The improvement according to claim 1 wherein the immunoassay is for the determination of an antibody or antigen.

12. In a method of determining a ligand or receptor in solution which comprises an assay wherein:
 (a) The presence of said ligand or receptor in said solution causes a conjugate in a solution to become matrix bound, said conjugate comprising a ligand or receptor labelled with a phosphatase;
 (b) The matrix bound conjugate is separated from unbound conjugate; and
 (c) The matrix bound or the unbound conjugate is assayed,
the improvement which compises:
 (d) Contacting the conjugate to be assayed with a phosphate of a nicotinamide adenine dinucleotide whereby a nicotinamide adenine dinucleotide is produced; and
 (e) Contacting the thus produced nicotinamide adenine dinucleotide with the components of a cyclic chemical reaction which is activated by the nicotinamide adenine dinucleotide, which cyclic chemical reaction interconverts said nicotinamide adenine dinucleotide and its reduced form and which thereby regenerates said nicotinamide adenine dinucleotide produced by the conjugate and produces a determinable change, said components of the cyclic chemical reaction being present in sufficient quantity to maintain the cyclic chemical reaction and produce determinable change as the cyclic chemical reaction proceeds, whereby amplification occurs.

13. The improvement according to claim 12 in which the determinable change results from the production of a determinable product.

14. The improvement according to claim 13 which employs a monoclonal antibody.

15. The improvement according to claim 14 wherein the conjugate comprises a monoclonal antibody.

16. The improvement according to claim 12 wherein the conjugate is a conjugate of an alkaline phosphatase.

17. The improvement according to claim 12 wherein NADP is converted to NAD by the conjugate and the NAD starts a cyclic chemical reaction which proceeds at pH 8.10–5 to interconvert NAD and NADH.

18. The improvement according to claim 17 in which the reduction of NAD to NADH is effected by a dehydrogenase.

19. The improvement according to claim 17 wherein the reductase is alcohol dehydrogenase.

20. The improvement according to claim 19 wherein the oxidation of NADH to NAD accompanies reduction of a tetrazolium compound whereby a colour change is produced.

21. The improvement according to claim 12 wherein the ligand or receptor is an antibody or antigen.

22. In a method of determining a ligand or receptor in solution which comprises an assay wherein:
 (a) A matrix to which is bound a ligand or receptor is contacted with a conjugate and with the solution, said conjugate comprising a ligand or receptor labelled with a phosphatase;
 (b) The matrix bound conjugate is separated from unbound conjugate; and
 (c) The matrix bound or the unbound conjugate is assayed,
the improvement which comprises:
 (d) Contacting the conjugate to be assayed with a phosphate of a nicotinamide adenine dinucleotide whereby a nicotinamide adenine dinucleotide is produced; and
 (e) Contacting the thus produced nicotinamide adenine dinucleotide with the components of a cyclic chemical reaction which is activated by the nicotinamide adenine dinucleotide, which cyclic chemical reaction interconverts said nicotinamide adenine dinucleotide and its reduced form and which thereby regenerates said nicotinamide adenine dinucleotide produced by the conjugate and produces a determinable change, said components of the cyclic chemical reaction being present in sufficient quantity to maintain the cyclic chemical reaction and produce determinable change as the cyclic chemical reaction proceeds, whereby amplification occurs.

23. The improvement according to claim 22 in which the determinable change results from the production of a determinable product.

24. The improvement according to claim 23 which employs a monoclonal antibody.

25. The improvement according to claim 24 wherein the conjugate comprises a monoclonal antibody.

26. The improvement according to claim 22 wherein the conjugate is a conjugate of an alkaline phosphatase.

27. The improvement according to claim 26 in which the reduction of NAD to NADH is effected by a dehydrogenase.

28. The improvement according to claim 27 wherein the reductase is alcohol dehydrogenase.

29. The improvement according to claim 28 wherein the oxidation of NADH to NAD accompanies reduction of a tetrazolium compound whereby a colour change is produced.

30. The improvement according to claim 26 wherein the ligand or receptor in solution and conjugate are added sequentially.

31. The improvement according to claim 30 wherein the ligand or receptor in solution is added before the conjugate.

32. The improvement according to claim 22 wherein NADP is converted to NAD by the conjugate and the NAD starts a cyclic chemical reaction which proceeds at pH 8-10.5 to interconvert NAD and NADH.

33. The improvement according to claim 22 wherein the ligand or receptor is an antibody or antigen.

* * * * *